(12) United States Patent
De Clercq et al.

(10) Patent No.: US 7,049,332 B2
(45) Date of Patent: May 23, 2006

(54) HIV INHIBITING N-AMINOIMIDAZOLE DERIVATIVES

(75) Inventors: Erik De Clercq, Lovenjoel (BE); Arthur Van Aerschot, Heist-op-den-Berg (BE); Piet Herdewijn, Wezemaal (BE); Irene Lagoja, Leuven (BE); Christophe Pannecoucque, Leuven (BE)

(73) Assignee: K. U. Leuven Research & Development, Leuven (BE), .

( * ) Notice: Subject to any disclaimer, the term of this patent is extended or adjusted under 35 U.S.C. 154(b) by 241 days.

(21) Appl. No.: 10/468,541

(22) PCT Filed: Feb. 23, 2001

(86) PCT No.: PCT/EP01/02140

§ 371 (c)(1),
(2), (4) Date: Feb. 11, 2004

(87) PCT Pub. No.: WO02/068395

PCT Pub. Date: Sep. 6, 2002

(65) Prior Publication Data

US 2004/0122024 A1    Jun. 24, 2004

(51) Int. Cl.
*A61K 31/415* (2006.01)
*C07D 233/38* (2006.01)

(52) U.S. Cl. .................................. 514/386; 548/331.1
(58) Field of Classification Search ............. 548/331.1; 514/386
See application file for complete search history.

(56) References Cited

FOREIGN PATENT DOCUMENTS

| EP | 0700911 A1 | 3/1996 |
| EP | 0786455 A1 | 7/1997 |
| HU | 219917 B | 9/1993 |

OTHER PUBLICATIONS

Lagoja, "Glycosylation of 1—Aminoimidazole—2(3H)—Thiones", Collect. Czech. chem. Commun., vol. 65,No. 7, 2000, pp. 1145-1155.

Schantl, "1—Arylamino- 1H—Imidazoles by 'Oxidative Reduction'—Conversion of 1—Arylamino—2,3—Dihydro-1H—Imidazole—2—Thiones", Heterocycles, vol. 48, No. 5, 1998, pp. 929-938.

Schantl, "Direct Synthetic Approach to N—Substituted 1—Amino- 2,3—Dihydro- 1H—Imidazole—2—Thiones", Hetrocycles, vol. 45, No. 4, 1997, pp. 691-700.

Salaski, Syntesis of Imidazobenzazepinthiones: A New Series of HIV—1 Reverse Transcriptase Inhibitors:, Tetrahedron Letters, vol. 36, No. 9, 1995, pp. 1387-1390.

Butler, "1,2,3—Triazolium- 1 -oxide, —1—imide and 1—methanide Hetero- 1, 3, 5- Triene Equilibrium: Ab Initio Calculations. A New Base Induced Ring Expansion of 1—Alkyl—1,2,3—triazolium Salts to 1, 2,3—Dihydro-1,2,4—triazines and 1—Amino—imidazoles via the 1,2,5—Triazahexa- 1,3,5—triene System. Azolium 1, 3—Dipoles", J. Chem. So. Perkin Trans. 1, 1992, pp. 147-152.

*Primary Examiner*—Deborah C. Lambkin
(74) *Attorney, Agent, or Firm*—Barnes & Thornburg LLP

(57) ABSTRACT

An N-aminoimidazole or N-aminoimidazolethione derivative, a pharmaceutically acceptable salt, a tautomer, an isomer, an ester or glycosylation product thereof, said derivative being represented by general formula (I): wherein m=zero or 1, n=zero or 1, $R^1$ is selected from hydrogen, methyl or ethyl, $R^2$ is selected from hydrogen, SH or —$SR^0$ wherein $R^0$ is methyl, benzyl or glucose residue; Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring, wherein the substitution is understood as being one or two substituents selected from H, F, Cl, Br, I, methyl, ethyl or isopropyl; L is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring wherein the substitution is understood as being one or two substituents selected from H, F, Cl, Br, I, methyl, ethyl or isopropyl. This invention further relates to the use of compounds of formula (I) as agents having biological activity, especially against viral infections.

18 Claims, 3 Drawing Sheets

SCHEME 1:

| | R⁶ | R¹ | R⁵ |
|---|---|---|---|
| 1 | phenyl, thienyl | methyl, ethyl, isopropyl | |
| 2 | phenyl, 3-br-phenyl, 4-br-phenyl, 3-cl-phenyl, 4-cl-phenyl, 4-methoxyphenyl, 3-CN-phenyl, 3-methoxycarbonylphenyl, methyl, methoxycarbonyl, thienyl | methyl, phenyl, methoxycarbonyl, | |
| 4 | | | 3,5-dimethylphenyl, 3-methoxyphenyl |

SCHEME 2

SCHEME 3:

SCHEME 4:

|  | $R^6$ | $R^1$ | $R^5$ | $R^0$ |
|---|---|---|---|---|
| 14.01 | $C_6H_5$ | $CH_3$ | 3-$ClC_6H_4$ | $CH_3$ |
| 14.02 | $C_6H_5$ | $CH_3$ | 3-$ClC_6H_4$ | $CH_2C_6H_5$ |

HIV INHIBITING N-AMINOIMIDAZOLE DERIVATIVES

The present invention relates to discovery of new N-aminoimidazole and N-aminoimidazole-thione derivatives. The invention further relates to compounds having HIV (Human Immunodeficiency Virus) replication inhibiting properties. The present invention also relates to compounds having antiviral activities with respect to other viruses, as well as compounds having antitumoral properties. The invention also relates to methods for preparation of all such compounds and pharmaceutical compositions comprising them. The invention further relates to the use of said compounds in the manufacture of a medicament useful for the treatment of subjects suffering from HIV infection, as well as for treatment of other viral, retroviral or lentiviral infections, treatment of animals suffering from FIV, viral, retroviral, lentiviral infections or treatment of tumour cells.

BACKGROUND OF THE INVENTION

It is well documented that the ability of HIV to rapidly evolve drug resistance, together with toxicity problems requires the development of additional classes of antiviral drugs: AICA-riboside [a) P. D. Cook, R. K. Robins, *J. Am. Chem. Soc.* 1976, 78, 1492; b) A. Yamazaki, M. Okutsu, *J. Heteroclycl. Chem.* 1978, 15, 3353; c) T. Kalman, D.Houston, *Nucleosides & Nucleotides* 1989, 8, 899; d) M. Wall, S. J. Benkovic, *J.Med.Chem.*, 1999, 42, 3421] (1-(-D-ribofuranosyl)-5-amino-4-imidazolecarboxamide) is an example of an open ring purine nucleoside showing potent antiviral activity. EICAR [A. Matsuda, T. Sasaki, T. Ueda, *Chem. Pharm. Bull.* 1988, 36, 2730] (5-alkynyl-1-D-ribof u rano-sylimidazole-4-carboxamide), likewise an imidazole derivative, shows a strong antileukemia activity. Also a bicyclic imidazole containing non-nucleoside derivative [E. J. Saloski, *Tetrahedron Lett.* 1995, 36, 1387] is reported as a HIV-1 reverse transcriptase inhibitor.

Many non nucleoside derivatives have been reported to inhibit proliferation of HIV and especially non-nucleoside reverse transcriptase inhibitors (NNRTI) make up a large part of these compounds. Excellent reviews describing these NNRTI can be found [a) M. Witvrouw et al., *AIDS*, 1999, 13, 1477–1483; b) E. De Clercq, *Il Farmaco* 1999, 54, 26–45]. A few N-aminoimidazolethione derivatives have been reported before and were obtained by a multistep reaction from α-halo-ketones, potassium thiocyanate and monosubstituted hydrazines [J. G. Schantl, I. M. Lagoja, *Heterocycles,* 1997, 45, 691].

However, there is still a need for compounds which either complement existing drugs such that the resulting cocktail has improved resistance to virus mutation or compounds which are themselves effective against many or all viable mutations of a virus.

SUMMARY OF THE INVENTION

The present invention relates to N-aminoimidazole and N-aminoimidazole-thione derivatives. The invention further relates to compounds having HIV (Human Immunodeficiency Virus) replication inhibiting properties. The present invention also relates to compounds having antiviral activities with respect to other viruses, as well as compounds having antitumoral properties. The invention also relates to methods for preparation of all such compounds and pharmaceutical compositions comprising them. The invention further relates to the use of said compounds in the manufacture of a medicament useful for the treatment of subjects suffering from HIV infection, as well as for treatment of other viral, retroviral or lentiviral infections, treatment of animals suffering from FIV, viral, retroviral, lentiviral infections or treatment of tumour or cancer cells.

One aspect of the present invention is the provision of N-aminoimidazole and N-aminoimidazolethione derivatives, compounds of formula (I) which effectively show antiviral properties, in particular against Human Immunodefiency Virus (HIV), which is the etiological agent of Acquired Immune Deficiency Syndrome (AIDS) in humans, and consequently may be useful for the treatment of individuals infected by HIV.

The present invention relates to the use of compounds of formula (I), pharmaceutically acceptable salts, tautomers, isomers, esters and glycosylation products thereof, wherein:

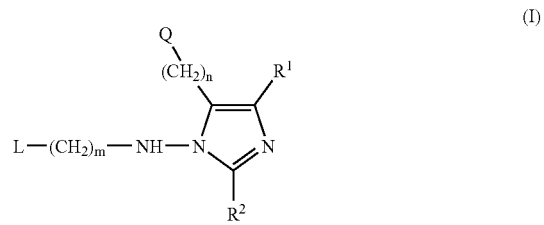

(I)

m is 1 or more preferably zero;
n is zero or 1;
$R^1$ is selected from hydrogen, methyl or ethyl;
$R^2$ is selected from hydrogen and —SH;
Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, carboxyl, aminocarbonyl, alkylamino-carbonyl, dialkylaminocarbonyl, phenylaminocarbonyl, alkyloxycarbonyl or phenyl;
  wherein alkyl is a methyl, ethyl, propyl or isopropyl and phenyl is a substituted or unsubstituted phenyl ring represented by the general formula (II)

(II)

wherein o is 1 or 2, and $R^3$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl; and L is selected from 1-naphtyl, 2-naphtyl, biphenyl, 2-pyridyl, 3-pyridyl, 4-pyridyl, 2-pyrimidyl, 4-pynmidyl, 5-pyrimidyl, thienyl, or a substituted or unsubstituted phenyl ring represented by the general formula (III)

(III)

wherein p is 1 or 2, and $R^4$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloakyl contains 1 to 4 haloatoms and alkyl is selected from methyl, ethyl, propyl or isopropyl, for the manufacture of a medicine or as a pharmaceutically active ingredient, especially as a virus replication inhibitor, preferably a retrovirus replication inhibitor or a non-nucleoside drug, for instance for the manufacture of a medicament or pharmaceutical composition having antiviral activity for the prevention and/or treatment of viral, preferably retroviral, infections in humans and mammals. The present invention further relates to a method of treatment of tumor or cancer cells in a mammal, including a human, comprising administering to the mammal in need of such treatment an effective amount of a compound of formula (I) as an active ingredient in admixture with at least a pharmaceutically acceptable carrier The present invention further relates to a method of treatment of a viral infection, preferably a retroviral infection in a mammal, including a human, comprising administering to the mammal in need of such treatment a therapeutically effective amount of a compound of formula (I) as an active ingredient, preferably in admixture with at least a pharmaceutically acceptable carrier.

The present invention also relates to compounds of formula (I) per se, their pharmaceutically acceptable salts, tautomers, isomers, esters and glycosylation products, with the further proviso that the said compound (I) is not selected from
- 1-(3-Chlorophenylamino)-2,3-dihydro-4-methyl-5-phenyl-1H-imidazole-2-thione;
- 1-(2-Chlorophenylamino)-2,3-dihydro-4-methyl-5-phenyl-1H-imidazole-2-thione;
- 1-(4-Chlorophenylamino)-2,3-dihydro-4-methyl-5-phenyl-1H-imidazole-2-thione;
- 1-(phenylamino)-2,3-Dihydro-4-methyl-5-phenyl-1H-imidazole-2-thione;
- 1-(4-nitrophenylamino)-2,3-dihydro-4-methyl-5-phenyl-1H-imidazole-2-thione;
- 1-(4-methylphenylamino)-2,3-dihydro-4-methyl-5-phenyl-1H-imidazole-2-thione;
- 1-(4-methyloxyphenylamino)-2,3-dihydro-4-methyl-5-phenyl-1H-imidazole-2-thione;
- 1-(benzylamino)-2,3-dihydro-4-methyl-5-phenyl-1H-imidazole-2-thione;
- 4-Methyl-5-phenyl-1-phenylamino-1H-imidazole;
- 4-Methyl-5-phenyl-1-(4-nitrophenyl)amino-1H-imidazole;
- 4-Methyl-5-phenyl-1-(4-chlorophenyl)amino-1H-imidazole;
- 4-Methyl-5-phenyl-1-(4-methylphenyl)amino-1H-imidazole; or
- 4-Methyl-5-phenyl-1-(4-methyloxyphenyl)amino-1H-imidazole.

The compounds of formula (I) will be designated as N-aminoimidazole derivatives when $R^2$ is hydrogen, and as N-aminoimidazolethione derivatives when $R^2$ is —SH. Reason for adopting the latter designation is because when $R^2$ is —SH, the thione functional group represented in formula (9) of FIG. 2 below is the readily available and well characterized tautomer of the —SH thiol group via a hydrogen shift from 4-C to 3-N.

The invention further relates to methods for the preparation of compounds of formula (I), to pharmaceutical compositions comprising them in admixture with at least a pharmaceutically acceptable carrier, the active ingredient preferably being in a concentration range of about 0.1–100% by weight, and to the use of these derivatives namely as non-nucleoside drugs useful for the treatment of subjects suffering from HIV infection.

The invention further relates to the use of a composition comprising:
(a) one or more derivatives of formula (I), and
(b) one or more retroviral enzyme inhibitors as biologically active agents in respective proportions such as to provide a synergistic effect against a viral infection, preferably a lentiviral infection and more preferably a retroviral infection in a mammal, for instance in the form of a combined preparation for simultaneous, separate or sequential use in retroviral infection therapy. Within the framework of this embodiment of the invention, the retroviral enzyme inhibitors used as a therapeutically active ingredients (b) may belong to categories already known in the art and include, among others:
- HIV integrase inhibitors such as are well known in the art,
- reverse transcriptase inhibitors such as for instance delavirdine, dideoxyadenosine, foscarnet sodium, stavudine, suramin sodium, zalcitabine and the like,
- Nucleoside reverse transcriptase inhibitors such as for instance zidovudine, lamivudine, didanosine and the like,
- Non-nucleoside reverse transcriptase inhibitors such as for instance nevirapine and the like,
- HIV protease inhibitors such as for instance saquinavir, ritonavir, indinavir, nelfinavir and the like.

When using a combined preparation of (a) and (b):
- the active ingredients (a) and (b) may be administered to the mammal (including a human) to be treated by any means well known in the art, i.e. orally, intranasally, subcutaneously, intramuscularly, intradermally, intravenously, intra-arterially, parenterally or by catheterization.
- the therapeutically effective amount of the combined preparation of (a) and (b), especially for the treatment of viral infections in humans and other mammals, preferably is a retroviral enzyme inhibiting amount. More preferably, it is a retroviral replication inhibiting amount of derivative (a) and a retroviral enzyme inhibiting amount of inhibitor (b). Still more preferably when the said retroviral enzyme inhibitor (b) is a protease inhibitor, its effective amount is a protease inhibiting amount. When the said retroviral enzyme inhibitor (b) is a reverse transcriptase inhibitor, its effective amount is a reverse transcriptase inhibiting amount. When the said retroviral enzyme inhibitor (b) is an integrase inhibitor, its effective amount is an integrase inhibiting amount.
- ingredients (a) and (b) may be administered simultaneously but it is also beneficial to administer them separately or sequentially, for instance within a relatively short period of time (e.g. within about 24 hours) in order to achieve their functional fusion in the body to be treated.

The invention also relates to the compounds of formula (I) being used for inhibition of the proliferation of other viruses than HIV, preferably the inhibition of viral activity of hepatitis B virus, hepatitis C virus or flaviviruses, with in particular yellow fever virus or Dengue virus.

The invention further relates to the compounds of formula (I) being able to reduce the proliferation of cells, especially tumour or cancer cells.

More generally, the invention relates to the compounds of formula (I) being useful as agents having biological activity (preferably antiviral or antitumoral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

The term "pharmaceutically acceptable salts" as used herein means the therapeutically active non-toxic acid addition salt forms which the compounds of formula (I) are able to form and which may conveniently be obtained by treating the base form of such compounds with an appropriate acid. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. This term also includes the solvates which the compounds of formula (I) as well as their salts are able to form, such as for example hydrates, alcoholates and the like.

The term "isomers" as used herein means all possible isomeric forms, including tautomeric forms, which the compounds of formula (I) may possess. Unless otherwise stated, the chemical designation of compounds denotes the mixture of all possible stereochemically isomeric forms, said mixtures containing all diastereomers and enantiomers (since the compounds of formula (1) may have at least one chiral center) of the basic molecular structure. More particularly, stereogenic centers may have either the R- or S-configuration, and substituents may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Consequently, if a mixture of enantiomers is obtained during any of the following preparation methods, it can be separated by liquid chromatography using a suitable chiral stationary phase. Suitable chiral stationary phases are, for example, polysaccharides, in particular cellulose or amylose derivatives. Commercially available polysaccharide based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like.

The terms cis and trans are used herein in accordance with Chemical Abstracts nomenclature and refer to the position of the substituents on a ring moiety. The absolute stereochemical configuration of the compounds of formula (I) may easily be determined by those skilled in the art while using well-known methods such as, for example, X-ray diffraction.

The term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$–$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings.

Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent form. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The compounds of formula (I) can be prepared while using a series of chemical reactions well known to those skilled in the art, altogether making up the process for preparing said compounds and exemplified further. The processes described further are only meant as examples and by no means are meant to limit the scope of the present invention.

DETAILED DESCRIPTION OF THE INVENTION

Materials and Preparation Methods

Figure 1:
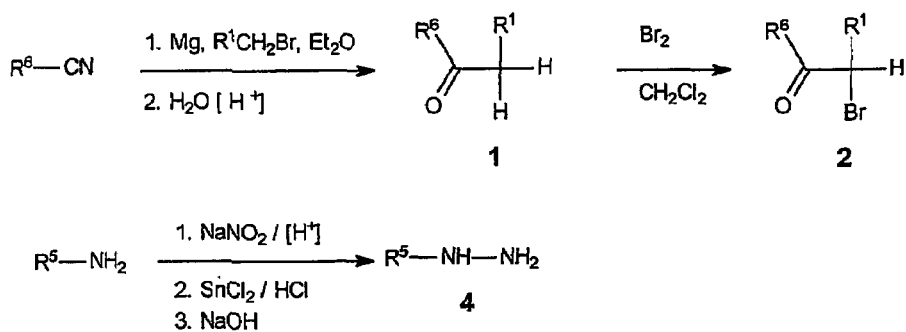
FIG. 1 shows scheme 1: General synthetic procedure for preparing respectively the starting bromoketones (2) and the hydrazine derivatives (4) for use with embodiments of the present invention, wherein $R^6$ is —$(CH_2)_n$-Q, $R^5$ is —$(CH_2)_m$-L and $R^1$, L, Q, m and n are as defined in formula (I).

Most starting materials are commercially available (e.g. from ACROS, Aldrich, Fluka). Commercially not available ketones (1) can be obtained via Grignard reaction of the corresponding nitrites through procedures well known in the art. The α-halo-ketones (2) can be synthesized by bromination of ketones (1) with bromine in dichloromethane. Using diazotation followed by reduction, hydrazines (4) can be obtained from the corresponding primary amines. The synthetic strategies are shown in scheme 1 of FIG. 1.

Figure 2:
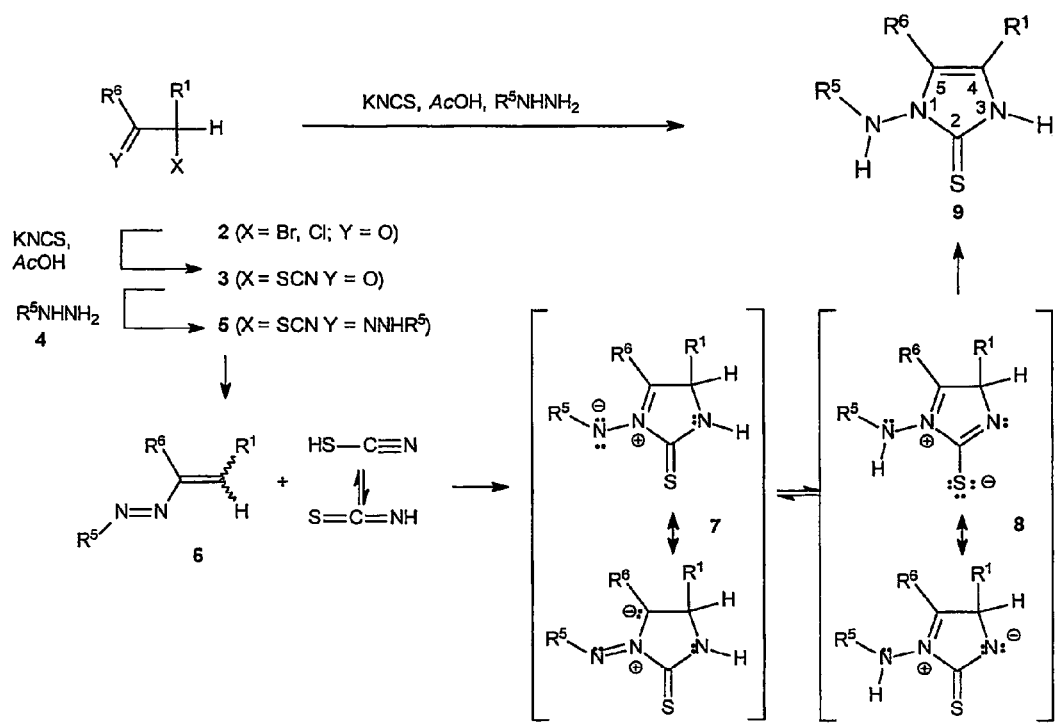
FIG. 2 shows scheme 2: General synthetic procedure for preparing the respective N-aminoimidazole-2-thiones (9) for use with embodiments of the present invention.

The compounds of formula (I) with $R^2$=SH, can be prepared by first reacting a α-haloketone (2) with an alkali thiocyanate such as potassium thiocyanate to obtain a thiocyanatoketone (3); the obtained thiocyanatoketone can be further reacted with a hydrazine derivative (4) into the hydrazone, which spontaneously will rearrange into the 1-amino-2-imidazolethione derivative (9) (compounds of formula (I) with $R^2$=SH). The corresponding synthetic strategies are shown in scheme 2 of FIG. 2. Compounds of formula (I) with $R^2$=H, can be obtained by desulfurizing the former obtained 1-amino-2-imidazolethione derivatives with e.g. hydrogen peroxide to obtain the 1-amino-imidazole derivatives of formula (I) with $R^2$=H (13). The corresponding synthetic strategy is shown in scheme 3 of FIG. 3.

Alternatively, the compounds of formula (I) with $R^2$=SH (9) can be obtained in a one pot procedure as outlined below.

Hereto, the α-halo-ketone (2) and alkali thiocyanate such as potassium thiocyanate can be first reacted in acetic acid, after which the monosubstituted hydrazine (4) is added to the resulting mixture at ambient temperature. For some combinations of reactants mild heating can be required to obtain the 1-amino-2-imidazolethione derivative (9) which can be isolated using standard procedures. The corresponding synthetic strategy is shown in scheme 2 of FIG. 2. Examples of compounds of formula (I) with $R^2$=SH obtained by this method are shown in table 1. Both alternatives may be summarized as a process for preparing a compound of formula (I), a pharmaceutically acceptable salt, a tautomer, an isomer, an ester or a glycosylation product thereof, comprising the steps of reacting an α-haloketone having the formula Q-$(CH_2)_n$—CO—$CHR_1X$, wherein Q, $R_1$ and n are as defined in formula (I) and X is a halogen atom, first with an alkali thiocyanate and then with a hydrazine derivative having the formula L-$(CH_2)_m$—$NHNH_2$, thereby obtaining an N-aminoimidazolethione derivative having the formula (I) wherein $R_2$ is —SH.

Prior research has been done to gain insight into the mechanism of this reaction. As already reported [J. G. Schantl, I. M. Lagoja, *Heterocycles*, 1997, 45, 691. ], this multistep reaction is considered to follow the path outlined in scheme 2 of FIG. 2. In a first step the α-halo-ketone (2) is reacted with an alkali thiocyanate such as potassium thiocyanate to obtain the thiocyanatoketone (3), which is converted by reaction with hydrazine (4) into the hydrazone (5). This hydrazone (5) easily can undergo a 1,4-elimination forming the corresponding azoalkene [J. G. Schantl, M. Prean, Monatsh. Chem. 1993, 124, 299. ] (6) and thiocyanic acid. These intermediates subsequently undergo a [3+2] cycloaddition reaction [J. G. Schantl, H. P. Kählig, M. Prean, *Heterocycles*, 1994, 37, 1873. ]. The azo-alkene (6) is serving as an isoelectronic hetero-allyl anion equivalent whereas the thiocyanic acid reacts as dipolarophile. The resulting heterocyclic azomethine imine intermediate (7) is anticipated to equilibrate with the zwitterion (8) by a proton transfer from the thiourea NH to the more basic exocyclic nitrogen atom. The 1-amino-2,3-dihydro-1H-imidazole-2-thione (9) is provided from a final 1,2-hydrogen shift from 4-C to 3-N.

Figure 3:
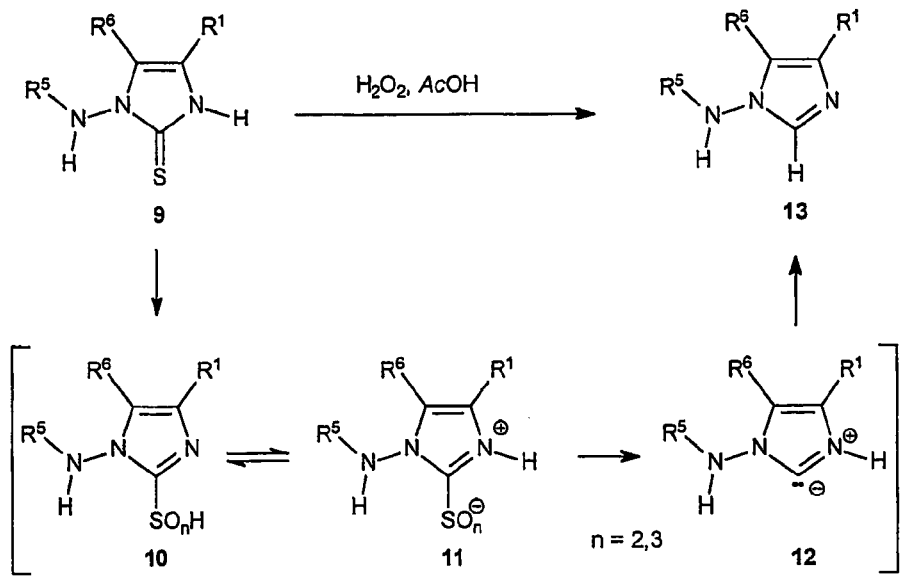
FIG. 3 shows scheme 3: General synthetic procedure for reducing the respective N-aminoimidazole-2-thiones (9) into N-aminoimidazole derivatives (13) for use with embodiments of the present invention.

The 1-amino-1H-imidazole derivatives (13) or compounds of formula (I) with $R^2$=H can be obtained with an oxidative reduction of the substituted 1-amino-2,3-dihydro-1H-imidazole-2-thiones (9) as shown in scheme 3 of FIG. 3. Examples of the imidazoles (13) derived by this method are reported in table 2. Desulfurization of thioureas has been achieved in the past by using Raney nickel [C. Temple, *J. Med. Chem.* 1990, 33, 656. ], nitric acid [J. Davoll, *J. Chem. Soc.* 1958, 1593. ], singlet oxygen [W. M. Abdou, M. M. Sidky, H. Wamhoff, *Z. Naturforsch., B.* 1987, 42, 1153. ], ozone [C. Crestini, E. Mincione, R. Saladino, R. Nicoletti, *Tetrahedron*, 1994, 50, 3259. ], ferric chloride [M. M. Fraser, R. A. Raphael, *J. Chem. Soc.* 1952, 226. ] or hydrogen peroxide [a) H. -J. Schönherr, H. -W. Wanzlick, *Chem. Ber,* 1970, 103, 1037; b) D. W. Karkhanis, L. Field, *Phosphorus Sulfur,* 1985, 22, 49; c) S. Grivas, E. Ronne, *Acta Chem. Scand.* 1995, 49, 225; d) J. G. Schantl, I. M. Lagoja, *Heterocycles,* 1998, 48, 929.].

A suitable procedure consists of treating a compound of formula (I) wherein $R^2$=SH (9) with 30% hydrogen peroxide at 10° C., selectively cleaving off the sulfur atom of the 2-thione function. As reported in prior art, hereby at first oxidation of the sulfur atom can take place (scheme 3, FIG. 3). Upon loss of $SO_n$ from the sulfonic acid intermediate (10) or possibly from the zwitterionic isomer (11), the resultant carbene-type intermediate (12) can undergo a proton shift to yield the 1-amino-1H-imidazole derivative (13).

Figure 4:
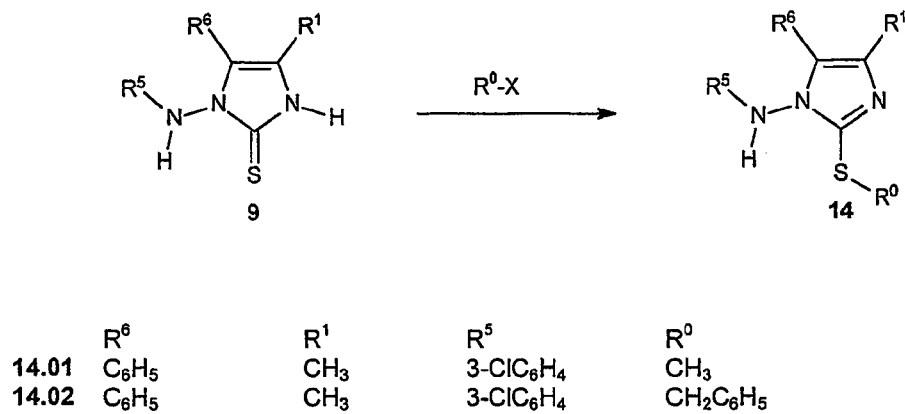
FIG. 4 shows scheme 4: General synthetic procedure for alkylating the respective N-aminoimidazole-2-thiones (9) into S-alkyl-N-aminoimidazole derivatives (14) for use with embodiments of the present invention.

Alkylation of 1-amino-2-imidazolethione derivative compounds 9 by means of an alkylating agent having the formula $R^0X$, wherein $R^0$ is e.g. methyl or benzyl, can quantitatively yield the S-alkyl derivatives (14). The reaction is shown in scheme 4 of FIG. 4. Under Mitsunobu conditions [D. L. Comins, G. Jianhua, *Tetrahedron Lett.* 1994, 35, 2819–2822. ] the S-alkyl-derivatives can also be obtained. Only in case of glycosylation by means of a glycosylating agent under Verbrueggen conditions, a temperature dependent S- or N-glycoslyation product can be formed [I. M. Lagoja, A. Van Aerschot, C. Hendrix, P. Herdewijn, *Collect. Czech. Chem. Commun.* 2000, 65, 1145–1155].

The following examples are provided for the purpose of illustrating the present invention and should in no way be interpreted as limiting the scope thereof.

EXAMPLES

A. General Methods

NMR spectra were recorded on a Varian, Gemini 200 spectrometer ($^1$H-200 MHz, $^{13}$C 50 MHz). All NH protons were assigned by exchange with $D_2O$. In case of AA'BB' systems determination of J is based on the assumption of an AB quartett [E. D. Becker in: "*High Resolution NMR, Theory and Chemical Application*", Academic Press, New York, 1969, 169. ] Exact mass measurements were performed on a quadrupole—time of flight mass spectrometer (Q-Tof-2, Micromass, Manchester, UK) equipped with a standard electrospray ionization (ESI) interface. Samples were infused in a 2-propanol: water (1:1) mixture at 3 mL/min. TLC was performed with TLC aluminum sheets (Merck, Silica gel 60 $F_{254}$) and silica (200–425 mesh) was used for column chromatography. Melting points (mp [° C.]) were determined with a Kofler-Bank.

All starting materials are commercially available (e.g. from ACROS, Aldrich, Fluka) or can be obtained as outlined further.

B. Intermediate Compounds

B.1. SYNTHESIS OF KETONES (1) FROM NITRILES VIA GRIGNARD REACTION: GENERAL PROCEDURE

In a 2-neck flask equipped with a reflux condenser and a dropping funnel a suspension of magnesium (2.83 g, 0.12 mol) and alkylbromide (0.12 mol) in dry ether were stirred under nitrogen. After addition of a crystal of iodine the reaction started. After the reaction was completed a solution of the nitrile (0.1 mol) in dry ether (15 mL) was added dropwise. Following heating under reflux for 6 hours the mixture was quenched with 6N $H_2SO_4$ ice (100 mL). To complete the hydrolysis of the ketimine the mixture was warmed and afterwards extracted with ether. After removing the solvent the resulting ketones could be used without further purification.

Isobutylphenylketone (1.01)

[Evans, Gordon, *J. Chem. Soc.* 1938, 1434, 1438.] Yield: quant; $^1$H-NMR (CDCl$_3$): 0.97, 1.00 (6H, 2×s, 2×CH$_3$), 2.29 (1 H, m, CH), 2.80 (2H, d, J=6.6 Hz, CH$_2$), 7.43–7.63 (3H, m, 3,4,5H Ar), 7.93 (2H, (d), 2,6H Ar).

Butyrophenone (1.02)

[H. Gilman, J. Eitsch, *J. Am. Chem. Soc.* 1957, 79, 2150–2153.] Yield: quant; $^1$H-NMR: 0.98 (3H, t, J=7.4 Hz, CH$_3$), 1.74 (2H, t×q, J=7.4 Hz, CH$_2$), 2.91 (2H, t, J=7.4 Hz, CH$_2$CO), 7.37–7.58 (3H, m, 3,4,5H Ar), 7.92 (2H, (d), 2,6H Ar).

Ethyl-2-thiophenylketone (1.03)

Yield: quant; $^1$H-NMR: 1.89 (3H, t, J=7 Hz, CH$_3$), 2.89 (2H, q, J=7 Hz, CH$_2$), 7.09 (1H, m, 4-H), 7.53–7.70 (2H, m, 3,5-H).

B.2. SYNTHESIS OF 3-CYANOPROPIOPHENONE

[H. R. Sonaware, N. S. Bellur, D. G.

Based on Kulkarni, N. R. Ayyangar, *Tetrahedron*, 1994, 50, 1243–1260.]: A mixture of 3-bromopropiophenone (10.65 g, 50 mmol), CuCN (5.82 g, 65 mmol) in DMF (35 mL) was heated under reflux for 6 h. After cooling the mixture to ambient temperature FeCl$_3$ (5 g) in H$_2$O (30 mL)/HCl conc (10 mL) was added and heated to 80° C. for another 20 min. After cooling to room temperature and extraction with ether further purification occurred by destination under reduced pressure (bp.: 140° C., 10 torr). The ketone could be obtained as slightly yellow, low melting (42° C.) solid.

3-Cyanopropiophenone (1.06)

Yield: 81%, $^1$H-NMR (CDCl$_3$): 1.29 (3H, t, J=7.2 Hz, CH$_3$), 3.11 (2H, q, J=7.2 Hz, CH$_2$), 7.69 (1H, (t), J~8 Hz, 5-H Ar), 7.90 (1H, d, J=7.6 Hz, 4-H Ar), 8.24 (1H, d, J=8.2 Hz, 6-H Ar), 8.29 (1H, s, 2-H Ar).

B.3. SYNTHESIS OF 3-METHOXYCARBONYLPROPRIOPHENONE

After refluxing 3-cyanopropiophenone 1.06 (3.5 g) with KOH (2.5 g) in ethanol (30 mL) for 2 hours the nitrile could be hydrolyzed to the corresponding acid derivative. Following removal of the solvent, dilution of the alkaline residue with water and acidification, the acid could be isolated, which was converted into the ester 1.07 by treatment with methanol (20 mL) and H$_2$SO$_4$ conc. (1 mL). After removing the solvent the residue was diluted with water and extracted with ethyl acetate. After drying the organic layer over Na$_2$SO$_4$ and removing the solvent the 3-methoxycarbonylpropiophenone 1.07 could be isolated in 85% yield over 2 steps.

3-Methoxycarbonylpropiophenone (1.07)

Yield: 85%, $^1$H-NMR (CDCl$_3$): 1.23 (3H, t, J=7.2 Hz, CH$_3$), 3.06 (2H, q, J=7.2 Hz, CH$_2$), 3.95 (3H, s, CH$_3$O), 7.58 (1H, (t), J~8 Hz, 5-H Ar), 8.20–8.27 (2H, m, 4,6-H Ar), 8.60 (1H, s, 2-H Ar).

B.4. SYNTHESIS OF α-HALO-kETONES: GENERAL PROCEDURE

To an ice-cooled solution of the corresponding ketone 1 (0.04 mol), bromine (0.04 mol, 2 mL) was added dropwise. The almost colorless solution was stirred at room temperature for another 20 min. After addition of aqueous NaHCO$_3$-solution (100 mL) the organic layer was separated and dried over Na$_2$SO$_4$. Following removal of the solvent the ketones could be used without further purification. In case of 3-cyanopropiophenone 1.06 in contrast the reaction needed to be heated under reflux.

α-Bromopropiophenone (2.01)

[N. De Kimpe, R. Verhe, L. De Buyck, N. Schamp, *J. Org. Chem.* 1980, 45, 2803–2813.1] Yield: quant; $^1$H-NMR (CDCl$_3$): 1.90 (3H, d, J=6.6 Hz, CH$_3$), 5.31 (1H, d, J=6.6 Hz, CH), 7.42–7.58 (3H, m, 3,4,5 H Ar), 8.00 (2H, (d), 2,6 H Ar).

α-Bromo-3'-bromopropiophenone (2.02)

[N. De Kimpe, R. Verhe, L. De Buyck, N. Schamp, *Tetrahedron Lett.*, 1980, 21, 2257–2260.]_Yield: quant; $^1$H-NMR (CDCl$_3$): 1.90 (3H, d, J=6.6 Hz, CH$_3$), 5.24 (1H, q, J=6.6 Hz, CH), 7.34 (1H, (t), J~7.8 Hz, 5-H Ar), 7.69 (1H, d, J=7.6 Hz, 4-H Ar), 7.92 (1H, d, J=7.8 Hz, 6-H Ar), 8.12 (1H, s, 2-H Ar).

α-Bromo-4'-bromopropiophenone (2.03)

[K. L. Nelson J. C. Robertson, J. J. Duvall *J. Am. Chem. Soc.* 1964, 86, 684–687.] Yield: quant; $^1$H-NMR (CDCl$_3$): 1.90 (3H, d, J=6.6 Hz, CH$_3$), 5.24 (1H, q, J=6.6 Hz, CH), 7.55, 7.60 (2H, 2,6H Ar)-7.83, 7.87 (2H, 3,5H Ar, AA'BB' J~8.2 Hz).

α-Bromo-3'chloropropiophenone (2.04)

[L. Szotyory, E. Hamburg, *J. Prakt. Chem.* 1963, 22, 202–213.] Yield: quant; $^1$H-NMR (CDCl$_3$): 1.89 (3H, d, J=6.6 Hz, CH$_3$), 5.25 (1H, q, J=6.6 Hz, CH), 7.41 (1H, (t), J~7.8 Hz, 5-H Ar), 7.55 (1H, d, J=7.6 Hz, 4-H Ar), 7.89 (1H, d, J=7.8 Hz, 6-H Ar), 7.96 (1H, s, 2-H Ar).

α-Bromo-4'-chloropropiophenone (2.05)

[B. L. Chenard, J. Bordner, T. W. Butler, L. K. Chambers, M. A. Collins, *J. Med. Chem.* 1995, 38, 3138–3145.] Yield: quant; $^1$H-NMR (CDCl$_3$): 1.91 (3H, d, J=6.6 Hz, CH$_3$), 5.25 (1H, q, J=6.6 Hz, CH), 7.43, 7.48 (2H, 2,6H Ar)-7.94, 7.99 (2H, 3,5H Ar, AA'BB' J~8.4 Hz).

α-Bromo-4'methoxypropiophenone (2.06)

[C. W. Perry M. V. Kalnins, K. H. Deitcher *J. Org. Chem.* 1972, 37, 4371–4376.] Yield: quant; $^1$H-NMR (CDCl$_3$): 1.88 (3H, d, J=6.6 Hz, CH$_3$), 3.84 (3H, s, CH$_3$O), 5.27 (1H, q, J=6.6 Hz, CH), 6.90, 6.95 (2H, 2,6H Ar)-7.96, 8.01 (2H, 3,5H Ar, AA'BB' J~8.2 Hz).

α-Bromophenylacetone (2.07)

[A. v. Wacek, K. Kratzl, A. v. Bezard, *Chem. Ber.* 1942, 75, 1348, 1352.] Yield: quant; $^1$H-NMR (CDCl$_3$): 2.27 (3H, s, CH$_3$), 5.44 (1H, s, CH), 7.33–7.46 (5H, m, Ar).

α-Bromobutyrophenone (2.08)

[N. De Kimpe, R. Verhe, L. De Buyck, N. Schamp, *Tetrahedron Lett.*, 1980, 21, 2257–2260. ] Yield: quant; $^1$H-NMR (CDCl$_3$): 1.08 (3H, t, J=7.4 Hz, CH$_3$), 2.18 (2H, q×d, J$^1$=6.6 Hz, J$^2$=7.4 Hz CH$_2$), 5.08 (1H, t, J=6.6 Hz), 7.47–7.62 (3H, m, 3,4,5H Ar), 8.02 (2H, (d), 2,6 H Ar).

α-Bromoisobutylphenylketone (2.09)

[E. G. Boswell, D. L. Musso, J. L. Kelley, F. E. Soroko, B. R. Cooper, *J. Heterocycl. Chem.* 1996, 33, 33–40. ] Yield: quant; $^1$H-NMR (CDCl$_3$): 1.05, 1.23 (6 H, 2×d, J=6.6 Hz, 2×CH$_3$), 2.47 (1H, m, CH), 5.01 (1H, d, J=8.4 Hz, CHC=O), 7.41–7.66 (5H, m, Ar).

α-Bromoacetylacetone (2.10)

[E. Bienvenue-Goetz, J. -E. Dubois, *J. Am. Chem. Soc.* 1981, 103, 5388–5392.] Yield: quant; $^1$H-NMR (CDCl$_3$): 2.36 (3H, s, CH$_3$), 3.75 (3H, s, CH$_3$O), 4.77 (1H, s, CH).

α-Bromo-2-ketobutyricacidmethylester (2.11)

[W. S. Lee, K. D. Nam, H. -G. Hahn, H. D. Mah, *J. Heterocycl. Chem.*, 1993, 30, 1105, 1110. ] Yield: quant; $^1$H-NMR (CDCl$_3$): 1.78 (3H, d, J=6.6 Hz, CH$_3$), 3.88 (3H, s, CH$_3$O), 5.15 (1H, q, J=6.6 Hz

α-Bromo-3'cyanopropiophenone (2.12)

[L. Villa et. al. *Farmaco Ed. Sci.* 1974, 29, 73–79. ] Yield: quant; $^1$H-NMR (CDCl$_3$): 1.94 (3H, d, J=6.4 Hz, CH$_3$), 5.30 (1H, q, J=6.4 Hz, CH), 7.66 (1H, (t), J~7.8 Hz, 5-H Ar), 7.90 (1H, d, J=6.6 Hz, 4-H Ar), 8.25 (1H, d, J=8 Hz, 6-H Ar), 8.31 (1H, s, 2-H Ar).

α-Bromo-3'methoxycarbonylpropiophenone (2.12)

Yield: quant; $^1$H-NMR (CDCl$_3$): 1.94 (3H, d, J=6.6 Hz, CH$_3$), 3.96 (3H, s, CH$_3$O), 5.31 (2H, q, J=6.6 Hz, CH$_2$), 7.62 (1H, (t), J~8 Hz, 5-H Ar), 8.20–8.28 (2H, m, 4,6-H Ar), 8.66 (1H, s, 2-H Ar).

α-Bromo-thiophenylethylketone (2.12)

Yield: quant; $^1$H-NMR (CDCl$_3$): 1.86 (2H, d, J=6.4 Hz, CH$_3$), 5.18 (1H, q, J=6.4 Hz, CH), 7.12 (1H, t, J=6 Hz, 4-H), 7.69 (1H, d, J=6 Hz, 3-H), 7.81 (1H, d, J=6 Hz, 5-H).

B.5. SYNTHESES OF N-MONOSUBTITUTED HYDRAZINES FROM ANILINES: GENERAL PROCEDURE

A suspension of the corresponding aniline (0.082 mol) was cooled to −10° C. A solution of NaNO$_2$ (5.7 g, 0.09 mol) in water (10 mL) was slowly added keeping the temperature always beyond −5° C. The red solution formed was stirred at −10° C. for another 30 min, after which a solution of SnCl$_2$ (47 g, 0.25 mol) in HCl$_{conc}$. (50 mL) was slowly added. A white precipitate was immediately formed. After the addition was completed the mixture was stored at 4° C. overnight and following filtration and washing with hexane the precipitate was suspended in 10% NaOH (200 mL). After extraction with ether, drying over Na$_2$SO$_4$ and removing the solvent, the obtained hydrazine could be used without further purification.

3,5-Dimethylphenylhydrazine (4.01)

[Borsche, Groth, *Just. Lieb. Ann. Chem.* 1941, 238–247. ] Yield: 72%; $^1$H-NMR (DMSO-d$_6$): 2.17 (6H, s, 2 CH$_3$), 3.90 (2H, s, br ex, NH$_2$), 6.25 (1H, s, 4-H Ar), 6.42 (2H, s, 2,6-H Ar), 6.65 (1H, s, br, ex, NH).

3-Methoxyphenylhydrazine (4.02)

[Kermack, Perkin, Robinson, *J. Chem. Soc.* 1921, 119, 1641. ] Yield: 74%; 3.67 (3H, s, CH$_3$O),), 3.90 (2H, s, br ex, NH$_2$), 6.13 (1H, d, J=8 Hz, 6-H Ar), 6.32–6.40 (2H, m, 2-H Ar, 4-H Ar), 6.63 (1H, s, br ex, NH), 6.97 (1H, (t), J=8 Hz, 5-H Ar).

B.6. SYNTHESIS OF 1-AMINO-2,3-DIHYDRO-1H-IMIDAZOLE-2-THIONES: GENERAL PROCEDURE

[J. G. Schantl, I. M. Lagoja, *Heterocycles,* 1997, 45, 691.]:

To a stirred solution of the α-halo ketone 2 (2.5 mmol) in acetic acid (10 mL) potassium thiocyanate (0.37 g, 3.8 mmol) was added at ambient temperature. After 30 min the hydrazine 4 (2.5 mmol) or hydrazine hydrochloride was added. Following stirring for 4 h at room temperature the reaction mixture was evaluated with TLC (CH$_2$Cl$_2$: MeOH=99:1). In case no product formation could be observed, the mixture was warmed to 80° C. for 2 h. After adding 30 mL of water the precipitate was filtered off and washed with water. Mostly recrystallization from methanol afforded pure products, only in some cases further purification by column chromatography (silica, CH$_2$Cl$_2$:MeOH=99: 1) was necessary.

B.7. SYNTHESIS OF 1-(3-CHLOROPHENYLAMINO)-2,3-DIHYDRO-4,5-DIPHENYL-1H-IMIDAZOLE-2-THIONE (9.26)

A mixture of benzoine (1.0 g, 0.0071 mol), KSCN (0.68 g, 0.0071 mol) and 3-chlorophenylhydrazine×HCl (1.26 g, 0.0071 mol) was stirred in acetic acid (10 mL) for two days. The white precipitate formed was filtered off (0.4 g). Water (50 mL) was added and the precipitate formed was filtered off. Recrystallization from MeOH/water (1:1) yielded 1.5 g (56%) of 9.26.

B.8. CONVERSION OF METHOXYCARBONYL GROUPS INTO THE FREE ACIDS

The corresponding methoxycarbonyl substituted imidadazoline-2-thione derivative (1.33 mmol) (9.27, 9.34, 9.35, respectively) was stirred in a 10% solution of NaOH (25 mL) for 6 h. After washing with CH$_2$Cl$_2$ removing impurities, the aqueous layer was acidified. The precipitate formed was filtered off and dried.

B.9. SYNTHESIS OF 5-(3-CARBOXAMIDOPHENYL)-1-(3-CHLOROPHENYLAMINO)-2,3-DIHYDRO-4-METHYL-1H-IMIDAZOLE-2-THIONE (9.38)

A mixture of the corresponding methoxycarbonyl substituted imidazoline-2-thione (9.34) (1.33 mmol) was stirred in NH$_3$/MeOH for 2 days. After removing the solvent the precipitate formed was recrystallized from MeOH/water (1:3) to yield 9.38 in 73% yield. $^1$H- and $^{13}$C-data of 1-amino-2,3-dihydro-1H-imidazoline-2-thiones 9 are collected in Tables 3 and 4 from which the 2-thione structure was deduced.

1-(3-Chlorophenylamino)-2,3-dihydro-4-methyl-5-phenyl-1H-imidazole-2-thione (9.01)

[I. M. Lagoja, A. Van Aerschot, C. Hendrix, P. Herdewijn, *Collect. Czech. Chem. Commun.* 2000, 65, 1145–1155.] Yield: 82 (%); mp: 215–217° C. (MeOH); Rf (CH$_2$Cl$_2$:MeOH=99:1): 0.55; Exact Mass (C$_{16}$H$_{15}$ClN$_3$S): Calcd.: 316.0675 [M+H]$^+$, Found: 316.0660.

1-(2-Chlorophenylamino)-2,3-dihydro-4-methyl-5-phenyl-1H-imidazole-2-thione (9.02)

[I. M. Lagoja, A. Van Aerschot, C. Hendrix, P. Herdewijn, *Collect. Czech. Chem. Commun.* 2000, 65, 1145–1155.] Yield: 86 (%); mp: 220–221° C. (MeOH); Rf (CH$_2$Cl$_2$:MeOH=99:1): 0.54; Exact Mass (C$_{16}$H$_{15}$ClN$_3$S): Calcd.: 316.0675 [M+H]$^+$, Found: 316.0703.

2,3-Dihydro-1-(4-fluorophenylamino)-4-methyl-5-phenyl-1H-imidazole-2-thione (9.03)

Yield: 68 (%); mp: 228° C. (MeOH); Rf (CH$_2$Cl$_2$:MeOH=99:1): 0.53; Exact Mass (C$_{16}$H$_{15}$FN$_3$S): Calcd.: 300.0971 [M+H]$^+$, Found: 300.0996.

1-(4-Chlorophenylamino)-2,3-dihydro-4-methyl-5-phenyl-1H-imidazole-2-thione (9.04)

[J. G. Schantl, I. M. Lagoja, *Heterocycles,* 1997, 45, 691.] Yield: 85 (%); mp: 212–214° C. (MeOH); Rf (CH$_2$Cl$_2$:MeOH=99:1): 0.54; Exact Mass (C$_{16}$H$_{15}$ClN$_3$S): Calcd.: 316.0675 [M+H]$^+$, Found: 316.0662.

5-(3-Bromophenyl)-1-(3-chlorophenylamino)-2,3-dihydro-4-methyl-1H-imidazole-2-thione (9.05)

Yield: 86 (%); mp: 196° C. (MeOH); Rf (CH$_2$Cl$_2$:MeOH=99:1): 0.52; Exact Mass (C$_{16}$H$_{14}$BrClN$_3$S): Calcd.: 393.9790 [M+H]$^+$, Found: 393.9839.

5-(4-Bromophenyl-1-(3-chlorophenylamino)-2,3-dihydro-4-methyl-1H-imidazole-2-thione (9.06)

Yield: 84 (%); mp: 220° C. (MeOH); Rf (CH$_2$Cl$_2$:MeOH=99:1): 0.52; Exact Mass (C$_{16}$H$_{14}$BrCN$_3$S): Calcd.: 393.9790 [M+H]$^+$, Found: 393.97788.

5-(3-Chlorophenyl)-1-(3-chlorophenylamino)-2,3-dihydro-4-methyl-1H-imidazole-2-thione (9.07)

Yield: 85 (%); mp: 204° C. (MeOH); Rf (CH$_2$Cl$_2$:MeOH=99:1): 0.52; Exact Mass (C$_{16}$H$_{14}$Cl$_2$N$_3$S): Calcd.: 350.0855 [M+H]$^+$, Found: 350.0271.

5-(4-Chlorophenyl)-1-(3-chlorophenylamino)-2,3-dihydro-4-methyl-1H-imidazole-2-thione (9.08)

Yield: 82 (%); mp: 225° C. (MeOH); Rf (CH$_2$Cl$_2$:MeOH=99:1): 0.52; Exact Mass (C$_{16}$H$_{14}$Cl$_2$N$_3$S): Calcd.: 350.0855 [M+H]$^+$, Found: 350.0356.

2,3-Dihydro-1-(3-chlorophenylamino)-5-(4-methoxyphenyl)-4-methyl-1H-imidazole-2-thione (9.09)

Yield: 88 (%); mp: 226° C. (MeOH); Rf (CH$_2$Cl$_2$:MeOH=99:1): 0.53; Exact Mass (C$_{17}$H$_{17}$ClN$_3$OS): Calcd.: 346.0781 [M+H]$^+$, Found: 350.0831.

1-(3-Chlorophenylamino)-2,3-dihydro-5-methyl-4-phenyl-1H-imidazole-2-thione(9.10)

Yield: 83 (%); mp: 238° C. (MeOH); Rf (CH$_2$Cl$_2$:MeOH=99:1): 0.53; Exact Mass (C$_{16}$H$_{15}$ClN$_3$S): Calcd.: 316.0675 [M+H]$^+$, Found: 316.0684.

1-(3-Chlorophenylamino)-2,3,4,5,6,7-hexahydro-1H-benzimidazole-2-thione (9.11)

Yield: 79 (%); mp: 148° C. (MeOH); Rf (CH$_2$Cl$_2$:MeOH=99:1): 0.52; Exact Mass (C$_{13}$H$_{15}$ClN$_3$S): Calcd.: 280.0675 [M+H]$^+$, Found: 280.0733.

2,3-Dihydro-4-methyl-5-phenyl-1-(phenylamino)-1H-imidazole-2-thione (9.12)

[J. G. Schantl, I. M. Lagoja, *Heterocycles,* 1997, 45, 691.] Yield: 92 (%); mp: 224–226° C. (MeO); Rf (CH$_2$Cl$_2$:MeOH=99:1): 0.49; Exact Mass (C$_{16}$H$_{15}$N$_3$S): Calcd.: 282.1065 [M+H]$^+$, Found: 282.1037.

2,3-Dihydro-1-(3,4-dimethylphenylamino)-4-methyl-5-phenyl-1H-imidazole-2-thione (9.13)

Yield: 62(%); mp: 228° C. (MeOH); Rf (CH$_2$Cl$_2$:MeOH=99:1): 0.53; Exact Mass (C$_{16}$H$_{20}$N$_3$S): 310.1378 [M+H]$^+$, Found: 310.1373.

1-(3-Bromophenylamino)-2,3-dihydro-4-methyl-5-phenyl-1H-imidazole-2-thione (9.14)

Yield: 52 (%); mp: 190° C. (MeOH); Rf (CH$_2$Cl$_2$:MeOH=99:1): 0.52; Exact Mass (C$_{16}$H$_{14}$BrN$_3$S): Calcd.: 360.0170 [M+H]$^+$, Found: 360.0168.

1-(3-Chloro-4-methylphenylamino)-2,3-dihydro-4-methyl-5-phenyl-1H-imidazole-2-thione (9.15)

Yield: 32 (%); mp: 190° C. (MeOH); Rf (CH$_2$Cl$_2$:MeOH=99:1): 0.52; Exact Mass (C$_{17}$H$_{16}$ClN$_3$S): Calcd.: 330.0832 [M+H]$^+$, Found: 330.0834.

1-(2,5)-Dichlorophenylamino)-2,3-dihydro-4-methyl-5-phenyl-1H-imidazole-2-thione (9.16)

Yield: 60 (%); mp: 266° C. (MeOH); Rf (CH$_2$Cl$_2$:MeOH=99:1): 0.54; Exact Mass (C$_{16}$H$_{14}$Cl$_2$N$_3$S): Calcd.: 350.0285 [M+H]$^+$, Found: 350.0248.

2,3-Dihydro-4-methyl-1-(3-nitrophenylamino)-5-phenyl-1H-imidazole-2-thione (9.17)

Yield: 48(%); mp: 214° C. (MeOH); Rf (CH$_2$Cl$_2$:MeOH=99:1): 0.49; Exact Mass (C$_{16}$H$_{14}$N$_2$O$_2$S): Calcd.: 327.0916 [M+H]$^+$, Found: 327.0928.

2,3-Dihydro-1-(3-fluorophenylamino)-4-methyl-5-phenyl-1H-imidazole-2-thione (9.18)

Yield: 36 (%); mp: 226° C. (MeOH); Rf (CH$_2$Cl$_2$: MeOH=99:1): 0.53; Exact Mass (C$_{16}$H$_{14}$FN$_3$S): Calcd.: 300.0971 [M+H]$^+$, Found: 300.0933.

2,3-Dihydro-4-methyl-1-(3-methylphenylamino)-5-phenyl-1H-imidazole-2-thione (9.19)

Yield: 58 (%); mp: 206° C. (MeOH); Rf (CH$_2$Cl$_2$: MeOH=99:1): 0.53; Exact Mass (C$_{17}$H$_{17}$N$_3$S): Calcd.: 296.1221 [M+H]$^+$, Found: 296.1208.

2,3-Dihydro-4,5-dimethyl-1-(3-chlorophenylamino)-1H-imidazole-2-thione (9.20)

Yield: 87 (%); mp: 234° C. (MeOH); Rf (CH$_2$Cl$_2$: MeOH=99:1): 0.54; Exact Mass (C$_{11}$H$_{13}$ClN$_3$S): Calcd.: 254.05187 [M+H]$^+$, Found: 254.0521.

2,3-Dihydro-4,5-dimethyl-1-(phenylamino)-1H-imidazole-2-thione (9.21)

Yield: 78 (%); mp: 217–219° C. (MeOH); Rf (CH$_2$Cl$_2$: MeOH=99:1): 0.53; Exact Mass (C$_{11}$H$_{14}$N$_3$S): Calcd.: 220.0908 [M+H]$^+$, Found: 220.0844.

2,3-Dihydro-4,5-dimethyl-1-(3-methylphenylamino)-1H-imidazole-2-thione (9.22)

Yield: 85 (%); mp: 230° C. (MeOH); Rf (CH$_2$Cl$_2$: MeOH=99:1): 0.54; Exact Mass (C$_{12}$H$_{16}$N$_3$S): Calcd.: 234.1065 [M+H]$^+$, Found: 234.1078.

2,3-Dihydro-4-isopropyl-1-(3-methylphenylamino)-5-phenyl-1H-imidazole-2-thione (9.23)

Yield: 46 (%); mp: 220–222° C. (MeOH); Rf (CH$_2$Cl$_2$: MeOH=99:1): 0.50; Exact Mass (C$_{19}$H$_{22}$N$_3$S): Calcd.: 324.1534 [M+H]$^+$, Found: 324.1524.

1-(3-Chlorophenylamino)-2,3-dihydro-4-ethyl-5-phenyl-1H-imidazole-2-thione (9.24)

Yield: 68 (%); mp: 116–118° C. (MeOH); Rf (CH$_2$Cl$_2$: MeOH=99:1): 0.52; Exact Mass (C$_{17}$H$_{17}$N$_3$ClS): Calcd.: 330.0831 [M+H]$^+$, Found: 330.0833.

2,3-Dihydro-4-ethyl-1-(3-methylphenylamino)-5-phenyl-1H-imidazole-2-thione (9.25)

Yield: 72 (%); mp: 202–204° C. (MeOH); Rf (CH$_2$Cl$_2$: MeOH=99:1): 0.53; Exact Mass (C$_{18}$H$_{20}$N$_3$S): Calcd.: 310.1377 [M+H]$^+$, Found: 310.1375.

1-(3-Chlorophenylamino)-2,3-dihydro-4,5-diphenyl-1H-imidazole-2-thione (9.26)

Yield: 56 (%); mp: 178–180° C. (MeOH); Rf (CH$_2$Cl$_2$: MeOH=99:1): 0.57; Exact Mass (C$_{21}$H$_{17}$N$_3$ClS): Calcd.: 378.0832 [M+H]$^+$, Found: 378.0863.

1-(3-Chlorophenylamino)-2,3-dihydro-5-methoxycarbonyl-4-methyl-1H-imidazole-2-thione (9.27)

Yield: 68 (%); mp: 194–196° C. (MeOH); Rf (CH$_2$Cl$_2$: MeOH=99:1): 0.49; Exact Mass (C$_{12}$H$_{13}$N$_3$O$_2$ClS): Calcd.: 298.0417 [M+H]$^+$, Found: 298.0421.

1-(3-Chlorophenylamino)-2,3-dihydro-5-hydroxycarbonyl-4-methyl-1H-imidazole-2-thione (9.28)

Yield: 52 (%); mp: 166–168° C. (MeOH); Rf (CH$_2$Cl$_2$: MeOH=99:1): 0.30; Exact Mass (C$_{11}$H$_{11}$N$_3$O$_2$ClS): Calcd.: 284.0261 [M+H]$^+$, Found: 284.0261.

1-(3-Chlorophenylamino)-2,3-dihydro-4-methoxycarbonyl-5-methyl-1H-imidazole-2-thione (9.29)

Yield 75 (%); mp: 160–162° C. (MeOH); Rf (CH$_2$Cl$_2$: MeOH=99:1): 0.45; Exact Mass (C$_{12}$H$_{13}$N$_3$O$_2$ClS): Calcd.: 298.0417 [M+H]$^+$, Found: 298.0410.

2,3-Dihydro-1-(3,5-dimethylphenylamino)-4-methyl-5-phenyl-1H-imidazole-2-thione (9.30)

Yield: 82 (%); mp: 240–242° C. (MeOH); Rf (CH$_2$Cl$_2$: MeOH=99:1): 0.53; Exact Mass (C$_{18}$H$_{20}$N$_3$S): Calcd.: 310.1378 [M+H]$^+$, Found: 310.1394.

1-(3-Methoxyphenylamino-2,3-dihydro-4-methyl-5-phenyl-1H-imidazole-2-thione (9.31)

Yield: 80 (%); mp: 184–186° C. (MeOH); Rf (CH$_2$Cl$_2$: MeOH=99:1): 0.53; Exact Mass (C$_{17}$H$_{18}$N$_3$OS): Calcd.: 312.1171 [M+H]$^+$, Found: 312.1188.

1-(3-Chlorphenylamino)-5-(3-cyanophenyl)-2,3-dihydro-4-methyl-1H-imidazole-2-thione (9.32)

Yield: 84 (%); mp: 168–170° C. (MeOH); Rf (CH$_2$Cl$_2$: MeOH=99:1) 0.53; Exact Mass (C$_{17}$H$_{14}$N$_4$ClS): Calcd.: 341.0628 [M+H]$^+$, Found: 341.0675.

5-(3-Cyanophenyl)-2,3-dihydro-4-methyl-1-(3-methylphenylamino-1H-imidazole-2-thione (9.33)

Yield: 88 (%); mp: 160–162° C. (MeOH); Rf (CH$_2$Cl$_2$: MeOH=99:1): 0.53; Exact Mass (C$_{19}$H$_{17}$N$_4$S): Calcd.: 321.1174 [M+H]$^+$, Found: 321.1152.

1-(3-Chlorphenylamino-2,3-dihydro-4-methyl-5-(3-methoxycarbonylphenyl-1H-imidazole-2-thione (9.34)

Yield: 90 (%); mp: 170–172° C. (MeOH); Rf (CH$_2$Cl$_2$: MeOH=99:1): 0.54; Exact Mass (C$^{18}$H$_{17}$N$_3$ClO$_2$S): Calcd.: 374.0730 [M+H]$^+$, Found: 374.0757.

2,3-Dihydro-4-methyl-1-(3-methylphenylamino)-5-(3-methoxycarbonylphenyl)-1H-imidazole-2-thione (9.35)

Yield: 80 (%); mp: 164–166° C. (MeOH); Rf (CH$_2$Cl$_2$: MeOH=99:1): 0.52; Exact Mass (C$_{19}$H$_{20}$N$_3$O$_2$S): Calcd.: 354.1276 [M+H]$^+$, Found: 354.1305.

1-(3-Chlorphenylamino)-2,3-dihydro-5-(3-hydroxy-carbonylphenyl)-4-methyl-1H-imidazole-2-thione (9.36)

Yield: 70 (%); mp: 170–172° C. (MeOH); Rf (CH$_2$Cl$_2$: MeOH=99:1): 0.34; Exact Mass (C$_{17}$H$_{15}$N$_3$ClO$_2$S): Calcd.: 360.0573 [M+H]$^+$, Found: 360.0608.

2,3-Dihydro-5-(3-hydoxycarbonylphenyl)-4-methyl-1-(3-methylphenylamino)-1H-imidazole-2-thione (9.37)

Yield: 61 (%); mp: 166–168° C. (MeOH); Rf (CH$_2$Cl$_2$: MeOH=99:1): 0.33; Exact Mass (C$_{18}$H$_{18}$N$_3$O$_2$S): Calcd.: 340.1119 [M+H]$^+$, Found: 340.1147.

5-(3-Carboxylamidophenyl)-1-(3-chlorphenylamino)-2,3-dihydro-4-methyl-1H-imidazole-2-thione (9.38)

Yield: 73 (%); mp: 164–166° C. (MeOH); Rf (CH$_2$Cl$_2$: MeOH=99:1): 0.35; Exact Mass (C$_{17}$H$_{16}$N$_4$OS): Calcd.: 359.0733 [M+H]$^+$, Found: 359.0702.

B.10. SYNTHESIS OF 1-ARYLAMINO-2,3-DIHYDRO-1H-IMIDAZOLES: GENERAL PROCEDURE

[J. G. Schantl, I. M. Lagoja, *Heterocycles*, 1998, 48, 929.]

A suspension of the respective 1-amino-2,3-dihydro-1H-imidazole-2-thione 9 (2 mmol) in glacial acetic acid (10 mL) was stirred in an ice-bad. Upon dropwise addition of 30% hydrogen peroxide (1 mL, 9.76 mmol) the reaction mixture cleared up resulting in a clear brown solution. After stirring for another 15 min the reaction mixture was made alkaline (pH 8–9) with 10% NaOH. The resulting precipitate was filtered off, washed with cold water and recrystallized from water.

B.11. SYNTHESIS OF 1-(ARYLAMINO)-5-(3-CARBOXAMIDOPHENYL)-4-METHYL-1H-IMIDAZOLINES FROM THE CORRESPONDING 1-(ARYLAMINO)-2,3-DIHYDRO-5-(3-METHOXYCARBONYLPHENYL)-4-METHYL-1H-IMIDAZOLE-2-THIONE

The corresponding methoxycarbonyl substituted imidadazoline-2-thione derivative (1.33 mmol) (9.34, 9.35, respectively) was treated with H$_2$O$_2$ (30%) in a 10% solution of NaOH (25 ml) for 6 h. After washing with CH$_2$Cl$_2$ to remove impurities, the aqueous layer was acidified. The precipitate formed was filtered off and dried.

$^1$H- and $^{13}$C-data imidazoles 13 are collected in Tables 5 and 6.

1-(3-Chlorophenylamino)-4-methyl-5-phenyl-1H-imidazole: (13.01)

Yield: 88 (%); mp: 218° C. (MeOH); Rf (CH$_2$Cl$_2$: MeOH=9:1): 0.82; Exact Mass (C$_{16}$H$_{15}$ClN$_3$): Calcd.: 284.0945 [M+H]$^+$, Found: 284.0955.

5-(3-Bromophenyl)-1-(3-chlorophenylamino)-4-methyl-1H-imidazole: (13.02)

Yield: 52 (%); mp: 164° C. (MeOH); Rf (CH$_2$Cl$_2$: MeOH=9:1): 0.85; Exact Mass (C$_{16}$H$_{13}$BrClN$_3$): Calcd.: 36.0059 [M+H]$^+$, Found: 362.0062.

5-(3-Chlorophenyl)-1-(3-chlorophenylamino)-4-methyl-1H-imidazole: (13.03)

Yield: 66 (%); mp: 168° C. (MeOH); Rf (CH$_2$Cl$_2$: MeOH=9:1): 0.83; Exact Mass (C$_{16}$H$_{13}$Cl$_2$N$_3$): Calcd.: 318.0565 [M+H]$^+$, Found: 318.0616.

1-(3-Chlorophenylamino)-4,5,6,7-tetrahydro-1H-benzimidazole (13.04)

Yield: 76 (%); mp: 180° C. (MeOH); Rf (CH$_2$Cl$_2$: MeOH=9:1): 0.76; Exact Mass (C$_{13}$H$_{14}$ClN$_3$): Calcd.: 248.0954 [M+H]$^+$, Found: 248.0953.

4-Methyl-5-phenyl-1-phenylamino-1H-imidazole: (13.05)

[J. G. Schantl, I. M. Lagoja, *Heterocycles*, 1998, 48, 929. ] Yield: 86 (%); mp: 165–167° C. (MeOH); Rf (CH$_2$Cl$_2$:MeOH=9:1): 0.84; Exact Mass (C$_{16}$H$_{16}$N$_3$): Calcd.: 250.1344 [M+H]$^+$, Found: 250.1322.

4,5-Dimethyl-1-phenylamino-1H-imidazole: (13.06)

[J. G. Schantl, I. M. Lagoja, *Heterocycles*, 1998, 48, 929. ] Yield: 67 (%); mp: 178° C. (MeOH); Rf (CH$_2$Cl$_2$: MeOH=9:1): $$ 0.76; Exact Mass (C$_{11}$H$_{13}$N$_3$): Calcd.: 188.1188 [M+H]$^+$, Found: 188.1153.

1-(3-Chlorophenylamino)-4,5-dimethyl-1H-imidazole: (13.07)

Yield: 82 (%); mp: 146° C. (MeOH); Rf (CH$_2$Cl$_2$: MeOH=9:1): 0.77; Exact Mass (C$_{11}$H$_{13}$ClN$_3$): Calcd.: 222.0798 [M+H]$^+$, Found: 222.0793.

4,5-Dimethyl-1-(3-methylphenylamino)-1H-imidazole: (13.08)

Yield: 86 (%); mp: 144° C. (MeOH); Rf (CH$_2$Cl$_2$: MeOH=9:1): 0.78; Exact Mass (C$_{12}$H$_{16}$N$_3$): Calcd.: 202.1344 [M+H]$^+$, Found: 202.1356.

4-Methyl-1-(3-methylphenylamino)-5-phenyl-1H-imidazole: (13.09)

Yield: 75 (%); mp: 159° C. (MeOH); Rf (CH$_2$Cl$_2$: MeOH=9:1): 0.84; Exact Mass (C$_{17}$H$_{18}$N$_3$): Calcd.: 264.1500 [M+H]$^+$, Found: 264.1536.

1-(4-Fluorophenylamino)-4-methyl-5-phenyl-1H-imidazole: (13.10)

Yield: 79 (%); mp: 155° C. (MeOH); Rf (CH$_2$Cl$_2$: MeOH=9:1): 0.76; Exact Mass (C$_{16}$H$_{15}$FN$_3$): Calcd.: 268.1250 [M+H]$^+$, Found: 268.1237.

4-Ethyl-1-(3-methylphenylamino)-5-phenyl-1H-imidazole: (13:11)

Yield: 81 (%); mp: 158–160° C. (MeOH); Rf (CH$_2$Cl$_2$: MeOH=9:1): 0.85; Exact Mass (C$_{18}$H$_{20}$N$_3$): Calcd.: 278.1657 [M+H]$^+$, Found: 278.1641.

1-(3-Chlorphenylamino)-5-methoxycarbonyl-4-methyl-1H-imidazole: (13.12)

Yield: 81 (%); mp: 138–140° C. (MeOH); Rf (CH$_2$Cl$_2$: MeOH=9:1): 0.85; Exact Mass (C$_{18}$H$_{20}$N$_3$): Calcd.: 278.1657 [M+H]$^+$, Found: 278.1641.

1-(3,5-Dimethylphenylamino)-4-methyl-5-phenyl-1H-imidazole (13.13)

Yield: 66 (%); mp: 154–156° C. (MeOH); Rf (CH$_2$Cl$_2$: MeOH=9:1): 0.86; Exact Mass (C$_{18}$H$_{20}$N$_3$): Calcd.: 278.1657 [M+H]$^+$, Found: 278.1636.

1-(3-Methoxyphenylamino)-4-methyl-5-phenyl-1H-imidazole (13.14)

Yield: 68 (%); mp: 156–158° C. (MeOH); Rf (CH$_2$Cl$_2$: MeOH=9:1): 0.84; Exact Mass (C$_{17}$H$_{18}$N$_3$O): Calcd.: 280.1450 [M+H]$^+$, Found: 280.1449.

1-(3-Chlorphenylamino)-5-(3-cyanophenyl)-4-methyl-1H-imidazole (13.15)

Yield: 75 (%); mp: 140–142° C. (MeOH); Rf (CH$_2$Cl$_2$: MeOH=9:1): 0.84; Exact Mass (C$_{17}$H$_{14}$N$_4$Cl): Calcd.: 309.0907 [M+H]$^+$, Found: 309.0911.

5-(3-Cyanophenyl)-4-methyl-1-(3-methylphenylamino)-1H-imidazole (13.16)

Yield: 70 (%); mp: 138–140° C. (MeOH); Rf (CH$_2$Cl$_2$: MeOH=9:1): 0.84; Exact Mass (C$_{18}$H$_{17}$N$_4$): Calcd.: 289.1453 [M+H]$^+$, Found: 289.1456.

5-(3-Carboxamidophenyl)-1-(3-chlorophenylamino)-4-methyl-1H-imidazole (13.17)

Yield: 84 (%); mp: 228–230° C. (MeOH); Rf (CH$_2$Cl$_2$: MeOH=9:1): 0.67; Exact Mass (C$_{17}$H$_{16}$N$_4$): Calcd.: 327.1013 [M+H]$^+$, Found: 327.1017.

5-(3-Carboxamidophenyl)-4-methyl-1-(3-methylphenylamino)-1H-imidazole (13.18)

Yield: 70 (%); mp: 220–222° C. (MeOH); Rf (CH$_2$Cl$_2$: MeOH=9:1): 0.66; Exact Mass (C$_{18}$H$_{19}$N$_4$O): Calcd.: 307.1556 [M+H]$^+$, Found: 307.1544.

1-(3-Chlorphenylamino)-5-(3-methoxycarbonylphenyl)-4-methyl-1H-imidazole (13.19)

Yield: 65 (%); mp: 172–174° C. (MeOH); Rf (CH$_2$Cl$_2$: MeOH=9:1): 0.80; Exact Mass (C$_{18}$H$_{17}$N$_3$ClO$_2$): Calcd.: 342.1009 [M+H]+, Found: 342.1015.

1-(3-Chlorphenylamino)-5-(3-hydroxycarbonylphenyl)-4-methyl-1H-imidazole (13.20)

Yield: 77 (%); mp: 176–178° C. (MeOH); Rf (CH$_2$Cl$_2$: MeOH=9:1): 0.63; Exact Mass (C$_{17}$H$_{15}$N$_3$ClO$_2$): 328.0853 [M+H]$^+$, Found: 328.0854.

B.12. PREPARATION OF 1-(3-CHLOROPHENYLAMINO)-4-METHYL-2-METHYLSULFANYL-5-PHENYL-1H-IMIDAZOLE (14.01)

A mixture of 1-(3-chlorophenylamino)-2,3-dihydro-4-methyl-5-phenyl-1H-imidazoline-2-thione (9.01) (0.1 g, 0.37 mmol) and methyl iodide (1.19 g, 8.40 mmol) in dichloromethane (5 mL) was heated under reflux for 1 h. Excess of methyl iodide and solvent were removed in vacuo. Further purification was achieved by recrystallisation from CH$_2$Cl$_2$/n-Hexane 1:1.

Yield: 98 (%); mp: 215° C. (MeOH); Rf (CH$_2$Cl$_2$: MeOH=9:1): 0.48; $^1$H-NMR (DMSO-d6, 200 MHz): δ=2.33 (3H, s, 4-Me), 2.73 (3H, s, S-Me), 6.37 (1H, d, J=8.0 Hz, 6-H, N—Ar), 6.49 (1H, s, 2-H, N—Ar), 6.75 (1H, d, J=7.6 Hz, 4-H, N—Ar), 7.67 (1H, dd, J$^1$=7.6 Hz, J$^2$=8.0 Hz, 5-H, N—Ar), 7.31–7.34 (5H, m, 5-Ph), 9.97 (NNH); $^{13}$C-NMR (DMSO-d6, 50 MHz): δ=9.1 (S-Me), 13.2 (4-Me), 126.2, 127.2, 127.9, 128.1 (1-C, 2,6-CH, 3,5-CH, 4-CH 5-Ph), 109.3, 110.8, 119.7, 129.1, 133.0, 144.5 (6-CH, 2-CH, 4-CH, 5-CH, 3-C, 1-C N—Ar), 123.1, 129.8, 144.8 (5-C, 4-C, 2-C imidazole); Exact Mass (C$_{17}$H$_{17}$ClN$_3$S): Calcd.: 330.0832 [M+H]$^+$, Found: 330.0837.

B.13. PREPARATION OF 2-BENZYLSULFANYL-1-(3-CHLOROPHENYLAMINO)-4-METHYL-5-PHENYL-1H-IMIDAZOLE (14.02)

A mixture of 1-(3-chlorophenylamino)-2,3-dihydro-4-methyl-5-phenyl-1H-imidazoline-2-thione (9.01) (0.2 g, 0.62 mmol) and benzylchloride (0.08 g, 0.62 mmol) in pyridine (5 mL) was heated under reflux for 3 h. After removing the solvent the crude product was purified by column chromatography (silica gel, ethyl acetate/hexane=2:1.

Yield: 97 (%); mp: 130° C. (MeOH); Rf (CH$_2$Cl$_2$: MeOH=9:1): 0.21; $^1$H-NMR (DMSO-d6, 200 MHz): δ=2.35 (3H, s, 4-Me), 4.12 (2H, s, CH$_2$S), 6.24 (1H, d, J=8.0 Hz, 6-H, N—Ar), 6.44 (1H, dd, J$^1$=7.6 Hz, J$^2$=8.0 Hz, 5-H, N—Ar), 6.55 (1H, s, 2-H, N—Ar), 6.83 (1H, d, J=7.6 Hz, 4-H, N—Ar), 7.02–7.33 (10H, m, 5H 5-Ph+5H S-Bn), 10.0 (1H, s, NNH); $^{13}$C-NMR (DMSO-d6, 50 MHz): δ=13.9 (4-Me), 39.0 (CH$_2$S), 127.6, 128.3, 129.1, 137.6 (4-CH, 2,6-CH, 3,5-CH, 1-C Bn), 127.7, 128.6, 128.8, 128.9, (4-CH, 2,6-CH, 3,5-CH, 1-C 5-Ph), 110.7, 112.8, 121.1, 130.3, 134.9, 140.6 (6-CH, 2-CH, 4-CH, 5-CH, 3-C, 1-C N—Ar), 130.2, 135.0, 147.9 (5-C, 4-C, 2-C imidazole); Exact Mass (C$_{23}$H$_{21}$ClN$_3$S): Calcd.: 406.1145 [M+H]$^+$, Found: 406.1165.

C. PHARMACOLOGICAL EXAMPLES

A rapid and automated assay procedure was used for the in vitro evaluation of anti-HIV agents. An HTLV-1 transformed T4-cell line MT-4, which was previously shown to be highly susceptible to and permissive for HIV infection, served as the target cell line. Inhibition of the HIV-induced cytopathogenic effect was used as the end point. The viabitlity of both HIV-and mock-infected cells was assessed spectrophotometrically via in situ reduction of 3-(4,5-dimethylthiazol-2-yl)-2,5-diphenyltetrazolium bromide (MTT). The 50% cytotoxic concentration ($CC_{50}$ in μg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in μg/ml). The ratio of $CC_{50}$ to $IC_{50}$ was defined as the selectivity index (SI). The compounds of formula (9 and 13) were shown to inhibit HIV effectively. Examples of $IC_{50}$, $CC_{50}$ and SI values for inhibition of proliferation of HIV by particular compounds of formula (I) are listed in table 7 herein below.

Examples of inhibition of cell proliferation by particular compounds of formula (I) can be found by looking at the respective $CC_{50}$ values in the MT-4 cell line.

Cells: MT-4 cells (Miyoshi et al., 1982) were grown and maintained in RPMI 1640 medium supplemented with 10% heat-inactivated fetal calf serum, 2 mM 1-glutamine, 0.1% sodium bicarbonate, and 20 œg of gentamicin per ml.

Viruses: The HIV-1(NL4.3) strain (Adachi et al., 1986) is a molecular clone obtained from the National Institutes of Health (Bethesda, Md.). The HIV-2(ROD) (Barr,-Sinoussi et al., 1983) stock was obtained from culture supernatant of HIV-2 infected cell lines.

References:
Adachi, A., Gendelman, H., Koenig, S., Folks, T., Willey, R., Rabson, A. and Martin, M (1986) Production of acquired immunodeficiency syndrome-associated retrovirus in human and nonhuman cells transfected with an infectious molecular clone, *J. Virol.*, 59, 284–291.
Barr-Sinoussi, F., Chermann, J. C., Rey, F., Nugeyre, M. T., Chamaret, S., Gruest, J., Dauguet, C., Axler-Blin, C., V,zinet-Brun, F., Rouzioux, C., Rozenbaum, W., Montagnier, L. (1983) Isolation of a T-lymphotropic retrovirus from patient at risk for AIDS, *Science* (Wash D.C.) 220, 868–871. Miyoshi, I., Taguchi, H., Kobonishi, I., Yoshimoto, S., Ohtsukj, Y., Shiraishi, Y. andAkagi,T. (1982) Type C virus-producing cell lines derived from adult T cell leukemia, *Gann mongr*, 28,219–228.

TABLE 7

Examples of $IC_{50}$, $CC_{50}$ and SI values for particular compounds 9 and 13

| Compound No | HIV-1 (NL4.3 WT) $IC_{50}$ (μg/ml) | SI | HIV-2 (ROD) $IC_{50}$ (μg/ml) | SI | cytotoxicity $CC_{50}$ (μg/ml) |
|---|---|---|---|---|---|
| 9.01 | 2.8 | 7.6 | 2.6 | 8.4 | 21.5 |
| 9.02 | 7.4 | 9.0 | >65 | <1 | 65 |
| 9.05 | 2.2 | 10.4 | 4.1 | 5.5 | 22.9 |
| 9.07 | 0.9 | 18.3 | 1.4 | 11.6 | 15.9 |
| 9.11 | 13.1 | 2.6 | >34.0 | <1 | 34.0 |
| 9.12 | 5.2 | 2.8 | >14.7 | <1 | 14.7 |
| 9.13 | 1.1 | 16.3 | >17.9 | <1 | 17.9 |
| 9.14 | 1.6 | 10.5 | >17.1 | <1 | 17.1 |
| 9.15 | 3.6 | 4.7 | >16.9 | <1 | 16.9 |
| 9.17 | 3.7 | 4.2 | >15.4 | <1 | 15.4 |
| 9.18 | 5.5 | 8.6 | >47.3 | <1 | 47.3 |
| 9.19 | 0.6 | 32.3 | >20.7 | <1 | 20.7 |
| 9.25 | 3.9 | 5.0 | >19.8 | <1 | 19.8 |
| 9.30 | 0.3 | 241.9 (Cryst)* | >65.3 | <1 | 65.3 |
| 9.31 | 3.1 | 4.0 | >12.3 | <1 | 12.3 |
| 9.32 | 13.8 | 2.3 | >32.1 | <1 | 32.1 |
| 13.01 | 0.5 | 6.0 | 0.5 | 6.9 | 3.25 |
| 13.02 | 0.5 | 6.7 | 0.3 | 9.5 | 3.13 |
| 13.03 | 0.2 | 73.5 | 0.23 | 63.8 | 14.7 |
| 13.09 | 1.4 | 5.6 | >7.6 | <1 | 7.6 |
| 13.15 | 3.4 | 3.2 | >10.9 | <1 | 10.9 |

*the compound crystallizes out during treatment at elevated concentrations, overestimating the toxic concentration.

TABLE 1

N-Aminoimidazole-2-thiones prepared according to the general procedure described in scheme 2.

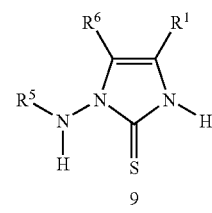

9

| | $R^6$ | $R^1$ | $R^5$ |
|---|---|---|---|
| 9.01 | $C_6H_5$ | $CH_3$ | 3-$ClC_6H_4$ |
| 9.02 | $C_6H_5$ | $CH_3$ | 2-$ClC_6H_4$ |
| 9.03 | $C_6H_5$ | $CH_3$ | 4-$FC_6H_4$ |
| 9.04 | $C_6H_5$ | $CH_3$ | 4-$ClC_6H_4$ |
| 9.05 | 3-$BrC_6H_4$ | $CH_3$ | 3-$ClC_6H_4$ |
| 9.06 | 4-$BrC_6H_4$ | $CH_3$ | 3-$ClC_6H_4$ |
| 9.07 | 3-$ClC_6H_4$ | $CH_3$ | 3-$ClC_6H_4$ |
| 9.08 | 4-$ClC_6H_4$ | $CH_3$ | 3-$ClC_6H_4$ |
| 9.09 | 4-$CH_3OC_6H_4$ | $CH_3$ | 3-$ClC_6H_4$ |
| 9.10 | $CH_3$ | $C_6H_5$ | 3-$ClC_6H_4$ |
| 9.11 | —$(CH_2)_4$— | | 3-$ClC_6H_4$ |
| 9.12 | $C_6H_5$ | $CH_3$ | $C_6H_5$ |
| 9.13 | $C_6H_5$ | $CH_3$ | 3-$CH_3$-4-$CH_3$—$C_6H_3$ |
| 9.14 | $C_6H_5$ | $CH_3$ | 3-$BrC_6H_4$ |
| 9.15 | $C_6H_5$ | $CH_3$ | 3-Cl-4-$CH_3C_6H_3$ |
| 9.16 | $C_6H_5$ | $CH_3$ | 2-Cl-5-$ClC_6H_3$ |
| 9.17 | $C_6H_5$ | $CH_3$ | 3-$NO_2C_6H_4$ |
| 9.18 | $C_6H_5$ | $CH_3$ | 3-$FC_6H_4$ |
| 9.19 | $C_6H_5$ | $CH_3$ | 3-$CH_3C_6H_4$ |
| 9.20 | $CH_3$ | $CH_3$ | 3-$ClC_6H_4$ |
| 9.21 | $CH_3$ | $CH_3$ | $C_6H_5$ |
| 9.22 | $CH_3$ | $CH_3$ | 3-$CH_3C_6H_4$ |
| 9.23 | $C_6H_5$ | $(CH_3)_2CH$ | 3-$CH_3C_6H_4$ |
| 9.24 | $C_6H_5$ | $CH_3CH_2$ | 3-$ClC_6H_4$ |
| 9.25 | $C_6H_5$ | $CH_3CH_2$ | 3-$CH_3C_6H_4$ |
| 9.26 | $C_6H_5$ | $C_6H_5$ | 3-$ClC_6H_4$ |
| 9.27 | $CH_3OCO$ | $CH_3$ | 3-$ClC_6H_4$ |
| 9.28 | COOH | $CH_3$ | 3-$ClC_6H_4$ |

TABLE 1-continued

N-Aminoimidazole-2-thiones prepared according to the general procedure described in scheme 2.

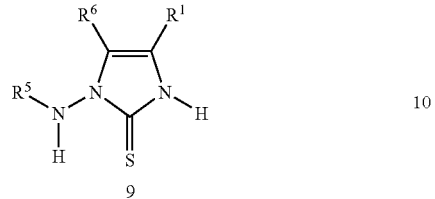

9

| | R⁶ | R¹ | R⁵ |
|---|---|---|---|
| 9.29 | CH₃ | CH₃OCO | 3-ClC₆H₄ |
| 9.30 | C₆H₅ | CH₃ | 3-CH₃-5-CH₃C₆H₃ |
| 9.31 | C₆H₅ | CH₃ | 3-CH₃OC₆H₄ |
| 9.32 | 3-CNC₆H₄ | CH₃ | 3-ClC₆H₄ |
| 9.33 | 3-CNC₆H₄ | CH₃ | 3-MeC₆H₄ |
| 9.34 | 3-MeOCOC₆H₄ | CH₃ | 3-ClC₆H₄ |
| 9.35 | 3-MeOCOC₆H₄ | CH₃ | 3-CH₃C₆H₄ |
| 9.36 | 3-HOCOC₆H₄ | CH₃ | 3-ClC₆H₄ |
| 9.37 | 3-HOCOC₆H₄ | CH₃ | 3-CH₃C₆H₄ |
| 9.38 | 3-NH₂COC₆H₄ | CH₃ | 3-ClC₆H₄ |

TABLE 3

$^1$H NMR N-Aminoimidazol-2-thiones 9 (DMSO-d6):

| | 4 Subst | 5 Subst | N-Ar | 1-NNH | 3-NH |
|---|---|---|---|---|---|
| 9.01 | 2.15(3H, s) | 7.34–7.38(5H, m) | 6.39(1H, d, J=8.4Hz, 6-H), 6.42(1H, s, 2-H), 6.74(1H, d, J=8Hz, 4-H), 7.12(1H, dd, J¹=8Hz, J²=8.4Hz, 5-H) | 9.30 | 12.55 |
| 9.02 | 2.15(3H, s) | 7.23–7.48(5H, m) | 6.08(1H, d, J=8Hz, 6-H), 6.72(1H, dd, J¹=8Hz, J²=8.8Hz, 4-H), 7.04(1H, dd, J¹=8Hz, J²=8.8Hz, 5-H), 7.23(1H, d, J=8Hz, 3-H) | 8.75 | 12.55 |
| 9.03* | 2.14(3H, s) | 7.32–7.38(5H, m) | 6.40, 6.44–6.91, 6.99(4H, AA'BB' A=3,5 H, B=2, 6 H, J=8.2Hz) | 8.94 | 12.49 |
| 9.04 | 2.14(3H, s) | 7.30–7.35(m, 5H) | 6.43, 6.47–7.12, 7.35(4H, AA'BB' A=3,5 H, B=2, 6 H; J=8.4Hz) | 9.18 | 12.54 |
| 9.05 | 2.16(3H, s) | 7.33–7.57(4H, m) | 6.39(2H, m, 6-H, 2-H), 6.76(1H, d, J=7.8Hz, 4-H), 7.14(1H, dd, J¹=7.8Hz, J²=8.2Hz, 5-H) | 9.31 | 12.61 |
| 9.06* | 2.14(3H, s) | 7.30, 7.34–7.57, 7.60 (4H, AA'BB' A=3, 5 H, B=2, 6 H; J=8.2Hz) | 6.38(2H, m, 6-H, 2-H), 6.75(1H, d, J=7.8Hz, 4-H), 7.12(1H, dd, J¹=7.8Hz, J²=8.2Hz, 5-H) | 9.31 | 12.60 |
| 9.07 | 2.16(3H, s) | 7.30–7.44(4H, m) | 6.40(2H, m, 6-H, 2-H), 6.75(1H, d, J=7.8Hz, 4-H), 7.13(1H, dd, J¹=7.8Hz, J²=8.2Hz, 5-H) | 9.31 | 12.61 |
| 9.08* | 2.14(3H, s) | 7.36, 7.40–7.43, 7.48 (4H, AA'BB' A=3, 5 H, B=2, 6 H; J=8.8Hz) | 6.41(2H, m, 6-H, 2-H), 6.75(1H, d, J=7.8Hz, 4-H), 7.08(1H, dd, J¹=7.8Hz, J²=8.2Hz, 5-H) | 9.31 | 12.58 |
| 9.09* | 2.11(3H, s) | 3.72(s, MeO) 6.90, 6.95–7.26, 7.30(4H, AA'BB' A=3,5 H, B=2,6 H; J=8.6Hz) | 6.38(2H, m, 6-H, 2-H), 6.73(1H, d, J=8Hz, 4-H), 7.12(1H, dd, J¹=8.3Hz, J²=8.2Hz, 5-H) | 9.25 | 12.45 |
| 9.10 | 7.34(1H, t, J=7.8Hz), 7.46(2H, dd, J¹=7.2Hz, J²=7.8Hz), 7.55, 7.60 (2H, d, J=7.2Hz) | 2.19(3H, s) | 6.52(1H, d, J=8.4Hz, 6-H), 6.56(1H, s, 2-H), 6.85(1H, d, J=8Hz, 4-H, 7.22(1H, dd, J¹=8Hz, J²=8.4Hz, 5-H) | 9.31 | 12.72 |
| 9.11 | | 1.70(4H, m, 5,6CH₂CH₂), 2.23(2H, m, 4-CH₂), 2.37(2H, m, 5-CH₂) | 6.44(2H, m, 6-H, 2-H), 6.81,(1H, d, J=8Hz, 4-H), 7.15(1H, dd, J¹=8.2Hz, J²=8Hz, 5-H) | 9.11 | 12.14 |
| 9.12 | 2.14(3H, s) | 7.30–7.37(5H, m) | 6.42(2H, d, J=8.4Hz, 2,6-H), 6.70(1H, t, J=7.6Hz, 4-H), 7.09(2H,(t), J=7.6Hz, 3, 5-H) | 8.95 | 12.47 |

TABLE 3-continued

¹H NMR N-Aminoimidazol-2-thiones 9 (DMSO-d6):

| | 4 Subst | 5 Subst | N-Ar | 1-NNH | 3-NH |
|---|---|---|---|---|---|
| 9.13 | 2.15(3H, s) | 7.31–7.40(5H, m) | 2.05(3H, s, 4-Me), 2.07(3H, s, 3-Me), 6.12(1H, d, J=8Hz, 6-H), 6.31(1H, s, 2-H), 6.84(1H, d, J=8.2Hz, 5-H) | 8.67 | 12.43 |
| 9.14 | 2.15(3H, s) | 7.30–7.36(5H, m) | 6.41(1H, d, J=8.4Hz, 6-H), 6.57(1H, s, 2-H), 6.87(1H, d, J=8Hz, 4-H), 7.06(1H, dd, J¹=8.4Hz J²=8Hz, 5-H) | 9.28 | 12.54 |
| 9.15 | 2.15(3H, s) | 7.32–7.38(5H, m) | 2.15(3H, s, 4-Me) 6.33(1H, d, J=8.4Hz, 6-H), 6.45(1H, s, 2-H), 7.06(1H, d, J=8.4Hz, 5-H) | 9.09 | 12.45 |
| 9.16 | 2.15(3H, s) | 7.30–7.46(5H, m) | 6.03(1H, d, J=2.4Hz, 6-H), 6.75(1H, d×d, J=2.4Hz, J=8.6Hz, 4-H), 7.26–7.30 (1H, m, 3-H) | 9.12 | 12.62 |
| 9.17 | 2.16(3H, s) | 7.36–7.44(5H, m) | 6.85(1H, d, J=7.8Hz, 6-H), 7.22(1H, s, 2-H), 7.36–7.44(1H, m, 5-H), 7.56(1H, d, J=7.8Hz, 4-H) | 9.71 | 12.45 |
| 9.18 | 2.19(3H, s) | 7.31–7.39(5H, m) | 6.12(1H,(d), 2-H), 6.27(1H,(d), 6-H), 6.52(1H,(t), 4-H), 7.07–7.19(1H, m, 5-H) | 9.43 | 12.59 |
| 9.19 | 2.15(3H, s) | 7.35–7.40(5H, m) | 2.48(3H, s, Me), 6.18(1H, d, J=8.2Hz, 6-H), 6.29(1H, s, 2-H), 6.52(1H, d, J=8.2Hz, 4-H), 6.97 (1H,(t), J=8.2Hz, 5-H) | 8.85 | 12.45 |
| 9.20 | 1.90(3H, s) | 2.01(3H, s) | 6.44(2H, m, 6-H, 2-H), 6.80,(1H, d, J=8Hz, 4-H), 7.18(1H, dd, J¹=8Hz, J²=8.4Hz, 5-H) | 9.13 | 12.80 |
| 9.21 | 1.89(3H, s) | 2.01(3H, s) | 6.47,(2H, d, J=8.2Hz, 2,6-H), 6.76(1H, t, J=7.4Hz, 4-H), 7.15(2H, dd, J¹=7.4Hz, J²=8.2Hz, 3,5-H) | 8.97 | 12.02 |
| 9.22 | 1.89(3H, s) | 2.02(3H, s) | 2.19(3H, s, Me) 6.24(1H, d, J=8.2Hz, 6-H), 6.32(1H, s, 2-H), 6.60(1H, d, J=8.2Hz, 4-H), 7.04 (1H,(t), J=8.2Hz, 5-H) | 8.70 | 12.00 |
| 9.23 | 1.21(6H,d, J=7Hz, 2×CH₃), 2.87(1H, q×q, J=7Hz, CH) | 7.32–7.36(5H, m) | 2.16(3H, s, Me) 6.14(1H, d, J=8.0Hz, 6-H), 6.29(1H, s, 2-H), 6.50(1H, d, J=8.0Hz, 4-H), 6.96 (1H,(t), J=8.0Hz, 5-H) | 8.76 | 12.50 |
| 9.24 | 1.17(3H, t, J=7.6Hz), 2.49(2H, q, J=7.6Hz) | 7.30–7.35(5H, m) | 6.40(2H, m, 6-H, 2-H), 6.73,(1H, d, J=8Hz, 4-H), 7.16(1H, dd, J¹=8.5Hz, J²=8Hz, 5-H) | 9.24 | 12.57 |
| 9.25 | 1.17(3H, t, J=7.6Hz), 2.49(2H, q, J=7.6Hz) | 7.28–7.34(5H, m) | 2.15(3H, s, Me) 6.13(1H, d, J=8.0Hz, 6-H), 6.28(1H, s, 2-H), 6.49(1H, d, J=8.0Hz, 4-H), 6.92 (1H,(t), J=8.0Hz, 5-H) | 8.81 | 12.48 |
| 9.26 | | 7.11–7.58(11H, m, Ph 4-C+Ph 5-C+5-H N-Ar) | 6.43(1H, d, J=8.0Hz, 6-H), 6.52(1H, s, 2-H), 6.78,(1H, d, J=8Hz, 4-H) | 9.29 | 13.03 |
| 9.27 | 3.64(3H, s, CH₃CO₂) | 2.35(3H, s) | 6.47(2H, m, 6-H, 2-H), 6.77,(1H, d, J=8Hz, 4-H), 7.23(1H, dd, J¹=8.5Hz, J²=8Hz, 5-H) | 9.12 | 13.02 |
| 9.28 | 10.7(1H, s, br, OH) | 2.15(3H, s) | 6.44(2H, m, 6-H, 2-H), 6.75,(1H, d, J=8Hz, 4-H), 7.15(1H, dd, J¹=8.5Hz, J²=8Hz, 5-H) | 9.06 | 12.90 |
| 9.29 | 2.08(3H, s) | 3.67(3H, s, CH₃CO₂) | 6.74(2H, m, 6-H, 2-H), 6.85,(1H, d, J=8Hz, 4-H), 7.22(1H, dd, J¹=8.5Hz, J²=8Hz, 5-H) | 8.74 | 10.28 |
| 9.30 | 2.16(3H, s) | 7.32–7.37(5H, m) | 2.11(6H, s, 2×CH₃), 6.06(2H, s, 2,6-H), 6.35(1H, s, 4-H) | 8.76 | 12.43 |
| 9.31 | 2.15(3H, s) | 7.33–7.38(5H, m) | 3.63(3H, s, CH₃), 5.96(1H, s, 2H), 6.02 (1H, d, J=8.2Hz, 6-H), 6.30(1H, d, J=8.2Hz, 4-H), 7.00(1H,(t), J=8.2Hz, 5-H) | 8.95 | 12.47 |
| 9.32 | 2.18(3H, s) | 7.58–7.78(3H, m, 4,5,6-H), 7.84 (1H, s, 2-H) | 6.42(2H, m, 6-H, 2-H), 6.74,(1H, d, J=8Hz, 4-H), 7.10(1H, dd, J¹=8.5Hz, J²=8Hz, 5-H) | 9.34 | 12.68 |
| 9.33 | 2.16(3H, s) | 7.57(1H,(t), J=7.6Hz, 5-H), 7.70–7.77(2H, m, 4,6-H), 7.86 (1H, s, 2-H) | 2.18(3H, s, Me) 6.18(1H, d, J=8.2Hz, 6-H), 6.31(1H, s, 2-H), 6.54(1H, d, J=8.2Hz, 4-H), 6.98 (1H,(t), J=8.2Hz, 5-H) | 8.93 | 12.60 |
| 9.34 | 2.17(3H, s) | 3.80(3H, s, MeCO₂) 7.54(1H,(t), J=7.6Hz, 5-H), 7.66(1H, d, J=8Hz, 6-H), 7.90 (1H, d, J=7.6Hz, 4-H), 7.94 (1H, s, 2-H) | 6.42(2H, m, 6-H, 2-H), 6.74,(1H, d, J=8Hz, 4-H), 7.13(1H, dd, J¹=8.5Hz, J²=8Hz, 5-H) | 9.30 | 12.61 |
| 9.35 | 2.17(3H, s) | 3.79(3H, s, MeCO₂) 7.54(1H,(t), J=7.6Hz, 5-H), 7.66(1H, d, J=8Hz, 6-H), 7.90 (1H, d, J=7.6Hz, 4-H), 7.94 (1H, s, 2-H) | 2.22(3H, s, Me) 6.18(1H, d, J=8.1Hz, 6-H), 6.31(1H, s, 2-H), 6.54(1H, d, J=8.1Hz, 4-H), 6.98 (1H,(t), J=8.1Hz, 5-H) | 9.30 | 12.54 |

TABLE 3-continued

¹H NMR N-Aminoimidazol-2-thiones 9 (DMSO-d6):

| | 4 Subst | 5 Subst | N-Ar | 1-NNH | 3-NH |
|---|---|---|---|---|---|
| 9.36 | 2.16(3H, s) | 13.09(s, br COOH) 7.51(1H,(t), J=7.8Hz, 5-H), 7.62(1H, d, J=8Hz, 6-H), 7.87 (1H, d, J=7.6Hz, 4-H), 7.94 (1H, s, 2-H) | 6.40(2H, m, 6-H, 2-H), 6.74,(1H, d, J=8Hz, 4-H), 7.12(1H, dd, $J^1$=8.2Hz, $J^2$=8Hz, 5-H) | 9.33 | 12.60 |
| 9.37 | 2.15(3H, s) | 13.00(s, br COOH) 7.49(1H,(t), J=7.8Hz, 5-H), 7.63(1H, d, J=8Hz, 6-H), 7.85 (1H, d, J=7.6Hz, 4-H), 7.95 (1H, s, 2-H) | 2.17(3H, s, Me) 6.19(1H, d, J=8.1Hz, 6-H), 6.30(1H, s, 2-H), 6.52(1H, d, J=8.1Hz, 4-H), 6.95 (1H,(t), J=8.1Hz, 5-H) | 8.90 | 12.51 |
| 9.38 | 2.16(3H, s) | 10.20(s, br $CONH_2$) 7.54–63(2H, m, 5-H, 6-H), 7.87–7.93 (2H, m, 4-H, 2H) | 6.40(2H, m, 6-H, 2-H), 6.78,(1H, d, J=8Hz, 4-H), 7.10(1H, dd, $J^1$=8.2Hz, $J^2$=8Hz, 5-H) | 9.33 | 12.62 |

*determination of J is based on the assumption of an AB quartett [E. D. Becker in: "High Resolution NMR, Theory and Chemical Application", Academic Press, New York, 1969, 169.]

TABLE 4

¹³C NMR N-Aminoimidazol-2-thiones 9(DMSO-d6):

| | 4 Subst | 5 Subst | N-Ar | Imidazole |
|---|---|---|---|---|
| 9.01 | 10.1 | 127.6, 128.2, 128.6, 129.0 (1-C, 4-CH, 2,6-CH, 3,5-CH) | 111.2, 111.9, 119.1, 130.8, 133.6, 148.9(6-CH, 2-CH, 4-CH, 5-CH, 3-C, 1-C) | 120.2, 126.6, 161.8 (4-C, 5-C, 2-C) |
| 9.02 | 10.1 | 127.7, 128.1, 128.5, 129.1 (1-C, 4-CH, 2,6-CH, 3,5-CH) | 113.2, 117.3, 120.4, 127.8, 129.1, 142.8(6-CH, 2-C, 4-CH, 5-CH, 3-CH, 1-C) | 120.0, 126.7, 161.9 (4-C, 5-C, 2-C) |
| 9.03 | 10.1 | 127.8, 128.1, 128.5, 129.1 (1-C, 4-CH, 2,6-CH, 3,5-CH) | 113.8(d, $J^F$=7.6Hz), 115.5(d, $J^F$=23Hz), 143.8, 158.7(2,6-CH, 3,5-CH, 1-C, 4-C) | 120.0, 126.7, 161.7 (4-C, 5-C, 2-C) |
| 9.04 | 10.1 | 127.7, 128.1, 128.5, 129.1 (1-C, 4-CH, 2,6-CH, 3,5-CH) | 114.1, 122.9, 128.8, 146.3 (2,6-CH, 4-C, 3,5-CH, 1-C) | 120.0, 126.7, 161.8 (4-C, 5-C, 2-C) |
| 9.05 | 10.1 | 121.3, 128.0, 129.9, 130.7, 130.9, 131.3 (3-C, 1-C, 6-CH, 4-CH, 2-CH, 5-CH) | 111.2, 111.9, 119.3, 130.8, 133.7, 148.7(6-CH, 2-CH, 4-CH, 5-CH, 3-C, 1-C) | 121.7, 125.0, 162.1 (4-C, 5-C, 2-C) |
| 9.06 | 10.1 | 120.8, 126.8, 130.9, 131.6 (4-C, 1-C, 2,6-CH, 3,5-CH) | 111.2, 111.9, 119.3, 130.8, 133.7, 148.7(6-CH, 2-CH, 4-CH, 5-CH, 3-C, 1-C) | 121.6, 125.4, 162.0 (4-C, 5-C, 2-C) |
| 9.07 | 10.1 | 127.6, 128.0, 128.5, 129.6, 130.5, 133.2 (6-CH, 4-CH, 5-CH, 2-CH, 1-C, 3-C) | 111.2, 111.9, 119.3, 130.8, 133.7, 148.7 (6-CH, 2-CH, 4-CH, 5-CH, 3-C, 1-C) | 121.3, 125.1, 162.1 (4-C, 5-C, 2-C) |
| 9.08 | 10.1 | 126.5, 128.7, 130.7, 132.9 (4-C, 2,6-C, 3,5-C, 1-C) | 111.2, 111.9, 119.3, 130.8, 133.7, 148.7 (6-CH, 2-CH, 4-CH, 5-CH, 3-C, 1-C) | 120.7, 125.4, 162.0 (4-C, 5-C, 2-C) |
| 9.09 | 10.0 | 55.2($CH_3O$); 114.1, 119.3, 130.5, 159.2 (2,6-CH, 1-C, 3,5-CH, 159.2(4-C) | 111.1, 111.9, 119.0, 130.7, 133.6, 148.9(6-CH, 2-CH, 4-CH, 5-CH, 3-C, 1-C) | 119.8, 126.5, 161.4 (4-C, 5-C, 2-C) |
| 9.10 | 126.7, 127.7, 128.9, 129.0 (2,6-CH, 4-CH, 1-C, 3,5-CH) | 9.2 | 111.3, 112.1, 119.7, 130.0, 133.8, 148.8(6-CH, 2-CH, 4-CH, 5-CH, 3-C, 1-C) | 122.0, 124.0, 162.2 (4-C, 5-C, 2-C) |
| 9.11 | | 19.3, 20.2, 21.6, 21.8(7-$CH_2$, 4-$CH_2$, 5-$CH_2$, 6-$CH_2$) | 111.2, 112.1, 119.5, 130.9, 133.7, 149.2(6-CH, 2-CH, 4-CH, 5-CH, 3-C, 1-C) | 120.9, 125.0, 161.1 (4-C, 5-C, 2-C) |
| 9.12 | 10.1 | 127.9, 128.0, 128.5, 128.6 (1-C, 4-CH, 2,6-CH, 3,5-CH) | 112.5, 119.4, 129.1, 147.3 (2,6-CH, 4-CH, 3,5-CH, 1-C) | 119.9, 126.8, 161.8 (4-C, 5-C, 2-C) |
| 9.13 | 10.1 | 127.9, 128.0, 128.4, 129.1 (1-C, 4-CH, 2,6-CH, 3,5-CH) | 18.5(4-Me), 19.8(3-Me), 110.0, 114.1, 126.8, 129.9, 136.5, 145.4(6-CH, 2-CH, 4-C, 5-CH, 3-C, 1-C) | 119.7, 127.0, 161.8 (4-C, 5-C, 2-C) |
| 9.14 | 10.1 | 127.3, 128.2, 128.6, 129.0 (1-C, 4-CH, 2,6-CH, 3,5-CH) | 111.5, 114.8, 122.0, 122.1, 131.1, 149.0 (6-CH, 2-CH, 4-CH, 3-C, 5-CH, 1-C) | 120.2, 126.6, 161.8 (4-C, 5-C, 2-C) |
| 9.15 | 10.1 | 127.7, 128.1, 128.6, 129.0 (1-C, 4-CH, 2,6-CH, 3,5-CH) | 18.6(4-Me), 111.6, 112.6, 126.6, 131.6, 133.5, 146.7(6-CH, 2-CH, 4-C, 5-CH, 3-C, 1-C) | 120.1, 125.7, 161.7 (4-C, 5-C, 2-C) |
| 9.16 | 10.1 | 127.4, 128.3, 128.7, 129.1 (1-C, 4-CH, 2,6-CH, 3,5-CH) | 106.3, 114.1, 118.7, 130.6, 148.5, 148.7 (2-CH, 4-CH, 6-CH, 5-CH, 3-C, 1-C) | 120.4, 126.5, 161.8 (4-C, 5-C, 2-C) |
| 9.17 | 10.1 | 127.9, 128.0, 128.5, 129.1 (1-C, 4-CH, 2,6-CH, 3,5-CH) | 112.5, 115.8, 119.8, 131.0, 132.3, 143.9 (6-CH, 2-CH, 4-CH, 5-CH, 3-C, 1-C) | 120.3, 126.3, 161.8 (4-C, 5-C, 2-C) |

TABLE 4-continued $^{13}$C NMR N-Aminoimidazol-2-thiones 9(DMSO-d6):

| | 4 Subst | 5 Subst | N-Ar | Imidazole |
|---|---|---|---|---|
| 9.18 | 10.6 | 127.9, 128.0, 128.5, 129.1 (1-C, 4-CH, 2,6-CH, 3,5-CH) | 99.2(d, J$^F$=20Hz, 2-CH), 105.9(d, J$^F$=20Hz, 4-CH), 108.5(6-CH), 130.8 (d, J$^F$=10Hz, 5-CH), 149.4(d, J$^F$=10Hz, 1-C), 165.6(3-C) | 116.2, 127.6, 160.8 (4-C, 5-C, 2-C) |
| 9.19 | 10.1 | 128.2, 128.6, 128.7, 129.1 (1-C, 4-CH, 2,6-CH, 3,5-CH) | 21.3(3-Me) 109.6, 113.1, 120.3, 128.9, 138.1, 147.4 (6-CH, 2-CH, 4-CH, 5-CH, 3-C, 1-C) | 119.8, 126.9, 161.8 (4-C, 5-C, 2-C) |
| 9.20 | 9.2 | 7.8 | 111.1, 111.9, 119.1, 130.9, 133.8, 149.1(6-CH, 2-CH, 4-CH, 5-CH, 3-C, 1-C) | 117.7, 122.2, 160.8 (4-C, 5-C, 2-C) |
| 9.21 | 9.1 | 7.9 | 112.5, 119.8, 129.1, 147.5 (2,6-CH, 4-CH, 3,5-CH, 1-C) | 117.5, 122.4, 160.7 (4-C, 5-C, 2-C) |
| 9.22 | 9.13 | 7.9 | 21.3(3-Me) 109.7, 113.0, 120.7, 129.0, 138.3, 147.5 (6-CH, 2-CH, 4-CH, 5-CH, 3-C, 1-C) | 117.3, 122.4, 160.7 (4-C, 5-C, 2-C) |
| 9.23 | 21.8(2 × CH$_3$), 24.1(CH) | 128.3, 128.5, 129.5, 129.7 (4-CH, 2,6-CH, 1-C, 3,5-CH) | 21.3(3-Me) 109.5, 113.2, 120.3, 128.8, 138.0, 147.4 (6-CH, 2-CH, 4-CH, 5-CH, 3-C, 1-C) | 125.7, 127.9, 162.2 (4-C, 5-C, 2-C) |
| 9.24 | 13.7(CH$_3$), 17.6 (CH$_2$) | 127.6, 128.4, 128.6, 129.3 (1-C, 4-CH, 2,6-CH, 3,5-CH) | 111.1, 111.9, 119.1, 130.8, 133.6, 148.9 (6-CH, 2-CH, 4-CH, 5-CH, 3-C, 1-C) | 125.8, 126.3, 162.1 (4-C, 5-C, 2-C) |
| 9.25 | 13.8(CH$_3$), 17.6 (CH$_2$) | 127.9, 128.2, 128.5, 129.3. (1-C, 4-CH, 2,6-CH, 3,5-CH) | 21.3(3-Me) 109.6, 113.1, 120.3, 128.9, 138.1, 147.4 (6-CH, 2-CH, 4-CH, 5-CH, 3-C, 1-C) | 125.5, 126.5, 162.0 (4-C, 5-C, 2-C) |
| 9.26 | 126.5, 128.0, 129.3, 130.4 (2,6-CH, 4-CH, 1-C, 3,5-CH) | 127.8, 128.0, 128.5, 128.8 (1-C, 4-CH, 2,6-CH, 3,5-CH) | 111.2, 112.1, 119.3, 130.8, 133.6, 148.8 (6-CH, 2-CH, 4-CH, 5-CH, 3-C, 1-C) | 123.3, 126.3, 162.9 (4-C, 5-C, 2-C) |
| 9.27 | 51.2(CH$_3$), 164.6 (C=O) | 11.3 | 111.0, 111.7, 118.8, 130.2, 134.0, 148.6 (6-CH, 2-CH, 4-CH, 5-CH, 3-C, 1-C) | 115.7, 133.0, 158.0 (4-C, 5-C, 2-C) |
| 9.28 | 164.7(C=O) | 11.4 | 111.4, 112.2, 119.1, 130.6, 134.0, 149.2 (6-CH, 2-CH, 4-CH, 5-CH, 3-C, 1-C) | 116.8, 133.5, 159.2 (4-C, 5-C, 2-C) |
| 9.29 | 17.5 | 51.5(CH$_3$), 170.6(C=O) | 111.3, 111.9, 119.5, 131.0, 133.9, 149.4 (6-CH, 2-CH, 4-CH, 5-CH, 3-C, 1-C) | 119.4, 125.1, 162.6 (4-C, 5-C, 2-C) |
| 9.30 | 10.2 | 128.0, 128.4, 128.5, 129.1 (4-CH, 1-C, 2,6-CH, 3,5-CH) | 21.2(3,5 Me) 110.3, 121.4, 137.9, 147.4 (2,6-CH, 3,5-C, 4-CH, 1-C) | 119.7, 126.9, 161.8 (4-C, 5-C, 2-C) |
| 9.31 | 10.1 | 127.8, 128.0, 128.5, 129.1 (1-C, 4-CH, 2,6-CH, 3,5-CH) | 54.9(3MeO) 98.8, 104.6, 105.3, 129.9, 148.8, 160.2 (2-CH, 6-CH, 4-CH, 5-CH, 1-C, 3-C) | 119.9, 126.8, 161.9 (4-C, 5-C, 2-C) |
| 9.32 | 10.1 | 111.8, 118.6, 128.9, 129.9, 131.7, 132.2, 133.6 (3-C, CN, 1-C, 5-CH, 4-CH, 2-CH, 6-CH) | 111.2, 112.0, 119.4, 130.9, 133.7, 148.6 (6-CH, 2-CH, 4-CH, 5-CH, 3-C, 1-C) | 121.8, 124.6, 162.3 (4-C, 5-C, 2-C) |
| 9.33 | 10.1 | 111.7, 118.7, 129.2, 129.9, 131.6, 132.3, 133.6 (3-C, CN, 1-C, 5-CH, 4-CH, 2-CH, 6-CH) | 21.3(3-Me) 109.7, 113.2, 120.6, 128.9, 138.3, 147.0 (6-CH, 2-CH, 4-CH, 5-CH, 3-C, 1-C) | 121.5, 124.8, 162.4 (4-C, 5-C, 2-C) |
| 9.34 | 10.0 | 52.3(MeO), 166.0(CO) 127.2, 128.7, 129.2, 129.6, 130.7, 133.6 (1-C, 4-CH, 5-CH, 2-CH, 6-CH, 3-C) | 111.2, 112.0, 119.2, 130.8, 133.6, 148.8 (6-CH, 2-CH, 4-CH, 5-CH, 3-C, 1-C) | 121.0, 125.8, 162.1 (4-C, 5-C, 2-C) |
| 9.35 | 10.0 | 52.3(MeO), 166.0(CO) 127.2, 128.7, 129.1, 129.5, 131.3, 133.7 (1-C, 4-CH, 5-CH, 2-CH, 6-CH, 3-C) | 21.1(3-Me) 109.7, 113.2, 120.5, 128.9, 138.5, 147.0 (6-CH, 2-CH, 4-CH, 5-CH, 3-C, 1-C) | 121.0, 127.8, 162.2 (4-C, 5-C, 2-C) |
| 9.36 | 10.1 | 167.1(CO$_2$H) 128.0, 128.6, 128.9, 129.7, 131.3, 133.3 (4-CH, 1-C, 5-CH, 2-CH, 3-C, 6-CH) | 111.2, 112.1, 119.3, 130.8, 133.6, 148.8 (6-CH, 2-CH, 4-CH, 5-CH, 3-C, 1-C) | 120.9, 125.7, 162.0 (4-C, 5-C, 2-C) |
| 9.37 | 10.1 | 167.1(CO$_2$H) 128.2, 128.9, 129.4, 129.7, 131.2, 133.3 (4-CH, 1-C, 5-CH, 2-CH, 3-C, 6-CH) | 21.1(3-Me) 109.7, 113.3, 120.5, 128.9, 138.1, 147.3 (6-CH, 2-CH, 4-CH, 5-CH, 3-C, 1-C) | 121.0, 126.0, 162.0 (4-C, 5-C, 2-C) |

TABLE 4-continued

| 13C NMR N-Aminoimidazol-2-thiones 9(DMSO-d6): | | | |
|---|---|---|---|
| 4 Subst | 5 Subst | N-Ar | Imidazole |
| 9.38   10.1 | 165.9(CONH$_2$) 128.6, 129.2, 129.6, 130.8, 131.4, 133.5 (1-C, 4-CH, 2-CH, 5-CH, 3-C, 6-CH) | 111.2, 112.0, 119.2, 130.7, 133.6, 148.7 (6-CH, 2-CH, 4-CH, 5-CH, 3-C, 1-C) | 121.8, 126.3, 162.0 (4-C, 5-C, 2-C) |

TABLE 5

| 1H NMR N-Aminoimidazoles 13 (DMSO-d6): | | | | |
|---|---|---|---|---|
| 4 Subst | 5 Subst | N-Ar | 2-H | 1-NNH |
| 13.01 2.35(3H, s) | 7.42–7.49(5H, m) | 6.52(1H, d, J=8.2Hz, 6-H), 6.62(1H, s, 2-H), 6.86(1H, d, J=8Hz, 4-H), 7.17(1H, dd, J$^1$=8Hz, J$^2$=8.2Hz, 5-H) | 7.51 | 9.45 |
| 13.02 2.21(3H, s) | 7.31–7.55(4H, m) | 6.30(2H, m, 6-H, 2-H), 6.77(1H, d, J=8Hz, 4-H), 7.14(1H, dd, J$^1$=8.1Hz, J$^2$=8.3Hz, 5-H) | 7.81 | 9.65 |
| 13.03 2.23(3H, s) | 7.31–7.43(4H, m) | 6.30(2H, m, 6-H, 2-H), 6.76(1H, d, J=8.1Hz, 4-H), 7.14(1H, dd, J$^1$=8Hz, J$^2$=8.2Hz, 5-H) | 7.82 | 9.66 |
| 13.04 | 1.69(4H, m, 5,6-CH$_2$CH$_2$), 2.25(2H, m, 4-CH$_2$), 2.48(2H, m, 7-CH$_2$) | 6.35(2H, m, 6-H, 2-H), 6.83(1H, d, J=8Hz, 4-H), 7.22(1H, dd, J$^1$=8Hz, J$^2$=8.4Hz, 5-H) | 7.55 | 9.49 |
| 13.05 2.22(3H, s) | 7.28–7.37(5H, m) | 6.33(2H, d, J=8.2Hz, 2,6-H), 6.72(1H, t, J=7.3Hz, 4-H), 7.11(2H, dd, J$^1$=7.3, J$^2$=8.2Hz, 3,5H) | 7.72 | 9.36 |
| 13.06 1.89(3H, s) | 2.06(3H, s) | 6.36(1H, d, J=8.2Hz, 2,6-H), 6.81(t, J=7.3Hz, 4-H), 7.19(dd, J$^1$=7.3, J$^2$=8.2Hz) | 7.52 | 9.14 |
| 13.07 1.91(3H, s) | 2.07(3H, s) | 6.35(2H, m, 6-H, 2-H), 6.86(1H, d, J=8.1Hz, 4-H), 7.22(1H, dd, J$^1$=8Hz, J$^2$=8.4Hz, 5-H) | 7.56 | 9.43 |
| 13.08 1.89(3H, s) | 2.06(3H, s) | 2.48(3H, s, 3-Me) 6.15(1H, d, J=8.2Hz, 6-H), 6.23(1H, s, 2-H), 6.62(1H, d, J=8.2Hz, 4-H), 7.06(1H,(t), J=8.2Hz, 5-H) | 7.50 | 9.06 |
| 13.09 2.13(3H, s) | 7.30–7.33(5H, m) | 2.22(3H, s, 3-Me) 6.17(2H, m, 2-H, 6-H), 6.57(1H, d, J=8.2Hz, 4-H), 6.99(1H,(t), J=8.2Hz, 5-H) | 7.71 | 9.27 |
| 13.10 2.21(3H, s) | 7.28–7.37(5H, m) | 6.32–6.36, 6.91–7.00(AA' BB') | 7.74 | 9.31 |
| 13.11 1.17(3H, t, J=7.6Hz), 2.49 (2H, q, J=7.6Hz) | 7.25–7.34(5H, m) | 2.13(3H, s, Me) 6.09(1H, d, J=8.0Hz, 6-H), 6.19(1H, s, 2-H), 6.52(1H, d, J=8.0Hz, 4-H), 7.02(1H,(t), J=8.0Hz, 5-H) | 7.69 | 9.21 |
| 13.12 2.39(3H, s) | 3.78(3H, s) | 6.35(2H, m, 6-H, 2-H), 6.86(1H, d, J=8.1Hz, 4-H), 7.22(1H, dd, J$^1$=8Hz, J$^2$=8.4Hz, 5-H) | 7.95 | 9.19 |
| 13.13 2.21(3H, s) | 7.32–7.36(5H, m) | 2.09(6H, s, 2×CH$_3$), 5.98(2H, s, 2,6-H), 6.38 (1H, s, 4-H) | 7.66 | 9.25 |
| 13.14 2.22(3H, s) | 7.28–7.38(5H, m) | 3.62(3H, s, 3-MeO) 5.88(1H, s, 2-H), 5.95(1H, d, J=8.2Hz, 6-H), 6.34(1H, d, J=8.2Hz, 4-H), 7.02(1H,(t), J=8.2Hz, 5-H) | 7.73 | 9.35 |
| 13.15 2.24(3H, s) | 7.57(1H,(t) J=7.6Hz, 5-H), 7.72 (3H, m, 2,4,6-H) | 6.32(2H, m, 6-H, 2-H), 6.78(1H, d, J=7.6Hz, 4-H), 7.12(1H, dd, J$^1$=7.6Hz, J$^2$=8.4Hz, 5-H) | 7.86 | 9.72 |
| 13.16 2.18(3H, s) | 7.55(1H,(t) J=7.6Hz, 5-H), 7.71 (2H, m, 4,6-H), 7.79(1H, s, 2-H) | 2.13(3H, s, Me) 6.11(1H, d, J=8.0Hz, 6-H), 6.20(1H, s, 2-H), 6.53(1H, d, J=8.0Hz, 4-H), 7.00(1H,(t), J=8.0Hz, 5-H) | 7.84 | 9.32 |
| 13.17 2.29(3H, s) | 7.42(m, 4H), 7.90(2H, m) | 6.36(2H, m, 6-H, 2-H), 6.72(1H, d, J=7.8Hz, 4-H), 7.04(1H, dd, J$^1$=7.8Hz, J$^2$=8.4Hz, 5-H) | 7.88 | 10.11 |
| 13.18 2.29(3H, s) | 7.50(m, 4H), 7.84(2H, m) | 2.12(3H, s, Me) 6.24(1H, d, J=8.0Hz, 6-H), 6.27(1H, s, 2-H), 6.42(1H, d, J=8.0Hz, 4-H), 7.00(1H,(t), J=8.0Hz, 5-H) | 8.00 | 9.94 |
| 13.19 2.24 | 12.61(1H, s, br, COOH) 7.51(1H,(t), J=7.8Hz, 5-H), 7.60 (1H, d, J=8Hz, 6-H, 7.82(1H, d, J=7.6Hz, 4-H), 7.86(1H, s, 2-H) | 6.30(2H, m, 6-H, 2-H), 6.76(1H, d, J=8Hz, 4-H), 7.12(1H, dd, J$^1$=8.2Hz, J$^2$=8Hz, 5-H) | 7.92 | 9.69 |
| 13.20 2.24(3H, s) | 12.73(1H, s, br, COOH) 7.53(1H,(t), J=7.8Hz, 5-H), 7.64 (1H, d, J=8Hz, 6-H, 7.83(1H, d, J=7.6Hz, 4-H), 7.87(1H, s, 2-H) | 6.32(2H, m, 6-H, 2-H), 6.75(1H, d, J=8Hz, 4-H), 7.14(1H, dd, J$^1$=8.2Hz, J$^2$=8Hz, 5-H) | 7.93 | 9.68 |

*determination of J is based on the assumption of an AB quartett [E. D. Becker in: "High Resolution NMR, Theory and Chemical Application", Academic Press, New York, 1969, 169.]

TABLE 6

13C NMR N-Aminoimidazoles 13(DMSO-d6):

| | 4 Subst | 5 Subst | N-Ar | Imidazole |
|---|---|---|---|---|
| 13.01 | 10.5 | 127.3, 128.9, 129.8, 129.9 (4-C, 2,6-CH, 3,5-CH, 1-C) | 111.3, 112.3, 120.9, 131.1, 134.0, 147.7 (6-CH, 2-CH, 4-CH, 5-CH, 3-C, 1-C) | 125.0, 131.2, 136.4 (5-C, 4-C, 2-CH) |
| 13.02 | 13.2 | 121.8, 128.0, 130.4, 130.7, 131.2, 131.3 (3-C, 6-CH, 4-CH, 2-CH, 5-CH, 1-C) | 110.4, 111.2, 119.7, 131.2, 134.0, 149.5 (6-CH, 2-CH, 4-CH, 5-CH, 3-C, 1-C) | 126.0, 134.5, 137.9 (5-C, 4-C, 2-CH) |
| 13.03 | 14.2 | 127.5, 127.6, 128.4, 130.5, 130.9, 134.6 (6-CH, 4-CH, 5-CH, 3-CH, 1-C, 3-C) | 110.5, 111.2, 119.7, 131.3, 134.1, 149.5 (6-CH, 2-CH, 4-CH, 5-CH, 3-C, 1-C) | 126.1, 133.3, 137.9 (5-C, 4-C, 2-CH) |
| 13.04 | | 19.4, 22.3, 23.1, 24.2 (7-CH$_2$, 4-CH$_2$, 5-CH$_2$, 6-CH$_2$) | 110.9, 111.7, 119.9, 131.3, 134.1, 149.9 (6-CH, 2-CH, 4-CH, 5-CH, 3-C, 1-C) | 125.6, 134.8, 135.7 (5-C, 4-C, 2-CH) |
| 13.05 | 14.3 | 127.5, 128.5, 129.0, 132.0 (4-CH, 2,6-CH, 3,5-CH, 1-C) | 111.7, 119.9, 129.4, 148.4 (2,6-CH, 4-CH, 3,5-CH, 1-C) | 127.8, 133.4, 137.5 (5-C, 4-C, 2-CH) |
| 13.06 | 13.1 | 7.3 | 112.1, 120.2, 129.5, 148.4 (2,6-CH, 4-CH, 3,5-CH, 1-C) | 122.8, 131.5, 135.6 (5-C, 4-C, 2-CH) |
| 13.07 | 13.2 | 7.2 | 110.8, 111.4, 119.8, 131.3, 134.1, 149.9 (6-CH, 2-CH, 4-CH, 5-CH, 3-C, 1-C) | 122.6, 130.9, 135.5 (5-C, 4-C, 2-CH) |
| 13.08 | 13.2 | 7.3 | 21.3(3-Me) 109.4, 112.6, 121.1, 129.4, 138.7, 148.4 (6-CH, 2-CH, 4-CH, 5-CH, 3-C, 1-C) | 122.8, 131.4, 135.6 (5-C, 4-C, 2-CH) |
| 13.09 | 14.22 | 127.5, 128.5, 129.1, 129.8 (4-CH, 2,6-CH, 3,5-CH, 1-C) | 21.2(3-Me) 109.0, 112.3, 120.8, 129.3, 138.7, 148.4 (6-CH, 2-CH, 4-CH, 5-CH, 3-C, 1-C) | 126.2, 133.3, 137.5 (5-C, 4-C, 2-CH) |
| 13.10 | 14.2 | 127.5, 128.4, 129.0, 133.5 (4-CH, 2,6-CH, 3,5-CH, 1-C) | 113.1(d, J$^F$=7.6Hz), 115.8(d, J$^F$=23Hz), 154.2, 158.8(2,6-CH, 3,5-CH, 1-C, 4-C) | 128.7, 137.4, 144.8 (5-C, 4-C, 2-CH) |
| 13.11 | 14.31(CH$_3$) 20.8(CH$_2$) | 127.5, 128.4, 129.2, 129.2 4-CH, 2,6-CH, 3,5-CH, 1-C | 21.2(3-Me) 108.9, 112.2, 120.7, 129.3, 138.8, 148.4 (6-CH, 2-CH, 4-CH, 5-CH, 3-C, 1-C) | 127.4, 129.3, 137.5 (5-C, 4-C, 2-CH) |
| 13.12 | 21.0 | 59.7(CH$_3$O), 158.9(CO) | 110.8, 111.4, 119.8, 131.3, 134.1, 149.9 (6-CH, 2-CH, 4-CH, 5-CH, 3-C, 1-C) | 112.3, 141.9, 146.4 (5-C, 4-C, 2-CH) |
| 13.13 | 12.4 | 125.6, 126.7, 127.2, 127.4 4-CH, 2,6-CH, 3,5-CH, 1-C | 19.3(3,5 Me), 107.8, 119.9, 136.6, 146.7 (2,6-CH, 4-CH, 3,5-C, 1-C) | 126.0, 131.3, 135.6 (5-C, 4-C, 2-CH) |
| 13.14 | 14.2 | 127.5, 128.5, 129.0, 129.1 4-CH, 2,6-CH, 3,5-CH, 1-C | 54.9(OMe) 97.9, 104.4, 105.2, 130.3, 149.8, 160.5 (2-CH, 6-CH, 4-CH, 1-C, 3-C) | 127.8, 133.3, 137.5 (5-C, 4-C, 2-CH) |
| 13.15 | 14.1 | 118.7(CN) 111.8, 129.9, 130.2, 131.2, 132.1, 133.6 (3-C, 5-CH, 1-C, 4-CH, 2-CH, 6-CH) | 110.5, 111.3, 119.8, 131.2, 134.0, 149.3 (6-CH, 2-CH, 4-CH, 5-CH, 3-C, 1-C) | 125.6, 135.0, 138.2 (5-C, 4-C, 2-CH) |
| 13.16 | 14.2 | 118.7(CN) 111.7, 129.8, 130.5, 131.0, 132.1, 133.6 (3-C, 5-CH, 1-C, 4-CH, 2-CH, 6-CH) | 21.2(3-Me) 109.1, 112.4, 121.1, 129.3, 138.8, 148.0 (6-CH, 2-CH, 4-CH, 5-CH, 3-C, 1-C) | 125.9, 134.7, 138.3 (5-C, 4-C, 2-CH) |
| 13.17 | 10.1 | 167.2(CONH$_2$) 128.9, 128.9, 130.2, 130.6, 131.2, 133.5 (1-C, 4-CH, 2-CH, 5-CH, 3-C, 6-CH) | 111.5, 112.4, 120.4, 131.2, 134.0, 147.3 (6-CH, 2-CH, 4-CH, 5-CH, 3-C, 1-C) | 124.9, 126.1, 146.9 (5-C, 4-C, 2-CH) |
| 13.18 | 12.3 | 165.9(CONH$_2$) 128.9, 128.9, 130.2, 130.6, 131.2, 133.5 (1-C, 4-CH, 2-CH, 5-CH, 3-C, 6-CH) | 21.3(3-Me) 108.2, 11.6, 119.4, 129.3, 138.8, 148.0 (6-CH, 2-CH, 4-CH, 5-CH, 3-C, 1-C) | 124.9, 126.4, 145.8 (5-C, 4-C, 2-CH) |
| 13.19 | 14.0 | 52.3(MeO), 166.0(CO) 127.2, 128.7, 129.2, 129.6, 130.7, 133.6 (1-C, 4-CH, 5-CH, 2-CH, 6-CH, 3-C) | 111.9, 111.3, 119.3, 131.0, 133.6, 149.0 (6-CH, 2-CH, 4-CH, 5-CH, 3-C, 1-C) | 126.7, 129.8, 138.7 (5-C,4-C, 2-CH) |
| 13.20 | 14.0 | 167.2(CO$_2$H), 128.5, 128.9, 129.0, 129.8, 131.3, 133.3 (4-CH, 1-C, 5-CH, 2-CH, 3-C, 6-CH) | 110.5, 111.2, 119.7, 131.2, 134.0, 149.5 (6-CH, 2-CH, 4-CH, 5-CH, 3-C, 1-C) | 127.0, 129.7, 138.5 (5-C, 4-C, 2-CH) |

TABLE 2

Examples of N-aminoimidazoles (13) as prepared according to the general procedure described in scheme 3.

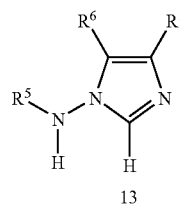

13

| | R$^6$ | R$^1$ | R$^5$ |
|---|---|---|---|
| 13.01 | C$_6$H$_5$ | CH$_3$ | 3-ClC$_6$H$_4$ |
| 13.02 | 3-BrC$_6$H$_4$ | CH$_3$ | 3-ClC$_6$H$_4$ |

TABLE 2-continued

Examples of N-aminoimidazoles (13) as prepared according to the general procedure described in scheme 3.

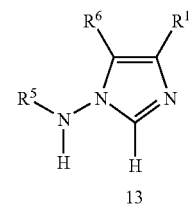

13

| | R$^6$ | R$^1$ | R$^5$ |
|---|---|---|---|
| 13.03 | 3-ClC$_6$H$_4$ | CH$_3$ | 3-ClC$_6$H$_4$ |
| 13.04 | | —(CH$_2$)$_4$— | 3-ClC$_6$H$_4$ |

TABLE 2-continued

Examples of N-aminoimidazoles (13) as prepared according to the general procedure described in scheme 3.

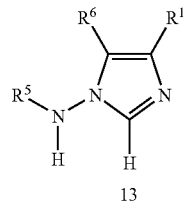

13

| | R⁶ | R¹ | R⁵ |
|---|---|---|---|
| 13.05 | C₆H₅ | CH₃ | C₆H₅ |
| 13.06 | CH₃ | CH₃ | C₆H₅ |
| 13.07 | CH₃ | CH₃ | 3-ClC₆H₄ |
| 13.08 | CH₃ | CH₃ | 3-CH₃C₆H₄ |
| 13.09 | C₆H₅ | CH₃ | 3-CH₃C₆H₄ |
| 13.10 | C₆H₅ | CH₃ | 4-FC₆H₄ |
| 13.11 | C₆H₅ | CH₃CH₂ | 3-CH₃C₆H₄ |
| 13.12 | CH₃OCO | CH₃ | 3-ClC₆H₄ |
| 13.13 | C₆H₅ | CH₃ | 3-CH₃-5-CH₃C₆H₃ |
| 13.14 | C₆H₅ | CH₃ | 3-CH₃OC₆H₄ |
| 13.15 | 3-CNC₆H₄ | CH₃ | 3-ClC₆H₄ |
| 13.16 | 3-CNC₆H₄ | CH₃ | 3-MeC₆H₄ |
| 13.17 | 3-NH₂COC₆H₄ | CH₃ | 3-ClC₆H₄ |
| 13.18 | 3-NH₂COC₆H₄ | CH₃ | 3-MeC₆H₄ |
| 13.19 | 3-MeOCOC₆H₄ | CH₃ | 3-ClC₆H₄ |
| 13.20 | 3-HOCOC₆H₄ | CH₃ | 3-ClC₆H₄ |

The invention claimed is:

1. An N-aminoimidazole or N-aminoimidazolethione derivative, a pharmaceutically acceptable salt, a tautomer, an isomer, an ester or a glycosylation product thereof said derivative being a compound represented by the general formula (I):

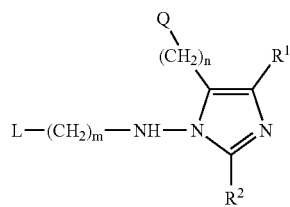

wherein:

m is zero or 1;

n is zero or 1;

$R^1$ is selected from hydrogen, methyl, ethyl, propyl or isopropyl;

$R^2$ is selected from hydrogen and —SH;

Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, carboxyl, aminocarbonyl, alkylamino-carbonyl, dialkylaminocarbonyl, phenylaminocarbonyl, alkyloxycarbonyl or phenyl;

wherein alkyl is a methyl, ethyl, propyl or isopropyl and phenyl is a substituted or unsubstituted phenyl ring represented by the general formula (II)

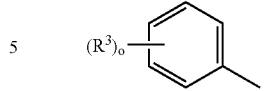

wherein o is 1 or 2, and $R^3$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl;

L is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring represented by the general formula (III)

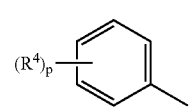

wherein p is 1 or 2, and $R^4$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl;

with the proviso that the compound (I) is not selected from
1-(3-Chlorophenylamino)-2,3-dihydro-4-methyl-5-phenyl-1H-imidazole-2-thione;
1-(2-Chlorophenylamino)-2,3-dihydro-4-methyl-5-phenyl-1H-imidazole-2-thione;
1-(4-Chlorophenylamino)-2,3-dihydro-4-methyl-5-phenyl-1H-imidazole-2-thione;
1-(phenylamino)-2,3-Dihydro-4-methyl-5-phenyl-1H-imidazole-2-thione;
1-(4-nitrophenylamino)-2,3-dihydro-4-methyl-5-phenyl-1H-imidazole-2-thione;
1-(4-methylphenylamino)-2,3-dihydro-4-methyl-5-phenyl-1H-imidazole-2-thione;
1-(4-methyloxyphenylamino)-2,3-dihydro-4-methyl-5-phenyl-1H-imidazole-2-thione;
1-(benzylamino)-2,3-dihydro-4-methyl-5-phenyl-1H-imidazole-2-thione;
4-Methyl-5-phenyl-1-phenylamino-1H-imidazole;
4-Methyl-5-phenyl-1-(4-nitrophenyl)amino-1H-imidazole;
4-Methyl-5-phenyl-1-(4-chlorophenyl)amino-1H-imidazole;
4-Methyl-5-phenyl-1-(4-methylphenyl)amino-1H-imidazole or
4-Methyl-5-phenyl-1-(4-methyloxyphenyl)amino-1H-imidazole.

2. A compound according to claim 1, wherein m and n equal zero;

Q is a substituted or unsubstituted phenyl ring represented by the general formula (II)

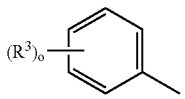

wherein o is 1 or 2, and R³ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl; and L is a substituted or unsubstituted phenyl ring represented by the general formula (III)

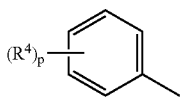

wherein p is 1 or 2, and R⁴ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl.

3. A compound according to claim 1, being selected from the following group consisting of:

2,3-Dihydro-1-(4-fluorophenylamino)-4-methyl-5-phenyl-1H-imidazole-2-thione;
5-(3-Bromophenyl)-1-(3-chlorophenylamino)-2,3-dihydro-4-methyl-1H-imidazole-2-thione;
5-(4-Bromophenyl)-1-(3-chlorophenylamino)-2,3-dihydro-4-methyl-1H-imidazole-2-thione;
5-(3-Chlorophenyl)-1-(3-chlorophenylamino)-2,3-dihydro-4-methyl-1H-imidazole-2-thione;
5-(4-Chlorophenyl)-1-(3-chlorophenylamino)-2,3-dihydro-4-methyl-1H-imidazole-2-thione;
2,3-Dihydro-1-(3-chlorophenylamino)-5-(4-methoxyphenyl)-4-methyl-1H-imidazole-2-thione;
1-(3-Chlorophenylamino)-2,3-dihydro-5-methyl-4-phenyl-1H-imidazole-2-thione;
2,3-Dihydro-1-(3,4-dimethylphenylamino)-4-methyl-5-Phenyl-1H-imidazole-2-thione;
1-(3-Bromophenylamino)-2,3-dihydro-4-methyl-5-phenyl-1H-imidazole-2-thione;
1-(3-Chloro-4-methylphenylamino)-2,3-dihydro-4-methyl-5-phenyl-1H-imidazole-2-thione;
1-(2,5-Dichlorophenylamino)-2,3-dihydro-4-methyl-5-phenyl-1H-imidazole-2-thione;
2,3-Dihydro-4-methyl-1-(3-nitrophenylamino)-5-phenyl-1H-imidazole-2-thione;
2,3-Dihydro-1-(3-fluorophenylamino)-4-methY1-5-phenyl-1H-imidazole-2-thione;
2,3-Dihydro-4-methyl-1-(3-methylphenylamino)-5-phenyl-1H-imidazole-2-thione;
2,3-Dihydro-4-isopropyl-1-(3-methylphenylamino)-5-phenyl-1H-imidazole-2-thione;
1-(3-Chlorophenylamino)-2,3-dihydro-4-ethyl-5-phenyl-1H-imidazole-2-thione;
2,3-Dihydro-4-ethyl-1-(3-methylphenylamino)-5-phenyl-1H-imidazole-2-thione;
1-(3-Chlorophenylamino)-2,3-dihydro-5-methoxycarbonyl-4-methyl-1H-imidazole-2-thione;
1-(3-Chlorophenylamino)-2,3-dihydro-5-hydroxycarbonyl-4-methyl-1H-imidazole-2-thione;
2,3-Dihydro-1-(3,5-dimethylphenylamino)-4-methY1-5-phenyl-1H-imidazole-2-thione;
1-(3-Methoxyphenylamino)-2,3-dihydro-4-methyl-5-phenyl-1H-imidazole-2-thione;
1-(3-Chlorphenylamino)-5-(3-cyanophenyl)-2,3-dihydro-4-methyl-1H-imidazole-2-thione;
5-(3-Cyanophenyl)-2,3-dihydro-4-methyl-1-(3-methylphenylamino)-1H-imidazole-2-thione;
1-(3-Chlorphenylamino)-2,3-dihydro-4-methyl-5-(3-methoxycarbonylphenyl)-1H-imidazole-2-thione;
2,3-Dihydro-4-methyl-1-(3-methylphenylamino)-5-(3-methoxycarbonyiphenyl)-1H-imidazole-2-thione;
1-(3-Chlorphenylamino)-2,3-dihydro-5-(3-hydroxycarbonylphenyl)-4-methyl-1H-imidazole-2-thione;
2,3-Dihydro-5-(3-hydroxycarbonylphenyl)-4-methyl-1-(3-methylphenylamino)-1H-imidazole-2-thione;
5-(3-Carboxylamidophenyl)-1-(3-chlorphenylamino)-2,3-dihydro-4-methyl-1H-imidazole-2-thione;
1-(3-Chlorophenylamino)-4-methyl-5-phenyl-1H-imidazole;
5-(3-Bromophenyl)-1-(3-chlorophenylamino)-4-methyl-1H-imidazole
5-(3-Chlorophenyl)-1-(3-chlorophenylamino)-4-methyl-1H-imidazole;
1-(3-Chlorophenylamino)-4,5-dimethyl-1H-imidazole;
4-Methyl-1-(3-methylphenylamino)-5-phenyl-1H-imidazole;
1-(4-Fluorophenylamino)-4-methyl-5-phenyl-1H-imidazole;
4-Ethyl-1-(3-methylphenylamino)-5-phenyl-1H-imidazole;
1-(3-Chlorphenylamino)-5-methoxycarbonyl-4-methyl-1H-imidazole;
1-(3,5-Dimethylphenylamino)-4-methyl-5-phenyl-1H-imidazole;
1-(3-Methoxyphenylamino)4-methyl-5-phenyl-1H-imidazole;
1-(3-Chlorophenylamino)-5-(3-cyanophenyl)-4-methyl-1H-imidazole;
5-(3-Cyanophenyl)-4-methyl-1-(3-methyiphenylamino)-1H-imidazole;
5-(3-Carboxamidophenyl)-1-(3-chlorphenylamino)-4-methyl-1H-imidazole;
5-(3-Carboxamidophenyl)-4-methyl-1-(3-methylphenylamino)-1H-imidazole;
1-(3-Chlorphenylamino)-5-(3-methoxycarbonylphenyl)-4-methyl-1H-imidazole;
1-(3-Chlorphenylamino)-5-(3-hydroxycarbonylphenyl)-4-methyl-1H-imidazole;

a pharmaceutically acceptable addition salt, or an ester thereof.

4. A process for preparing an N-aminoimidazolethione or N-aminoimidazole derivative, a pharmaceutically acceptable salt, a tautomer, an isomer, an ester or a glycosylation product thereof, said derivative being a compound represented by the general formula (I):

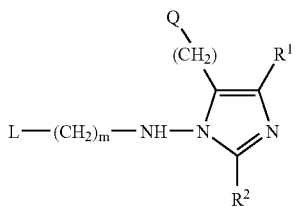

wherein:
- m is zero or 1;
- n is zero or 1;
- $R^1$ is selected from hydrogen, methyl, ethyl, propyl or isopropyl;
- $R^2$ is selected from hydrogen and —SH;
- Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, carboxyl, aminocarbonyl, alkylamino-carbonyl, dialkylaminocarbonyl, phenylaminocarbonyl, alkyloxycarbonyl or phenyl;
  - wherein alkyl is a methyl, ethyl, propyl or isopropyl and phenyl is a substituted or unsubstituted phenyl ring represented by the general formula (II)

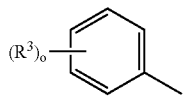

wherein o is 1 or 2, and $R^3$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl;
- L is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring represented by the general formula (III)

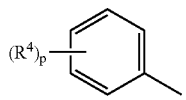

wherein p is 1 or 2, and $R^4$ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl;

with the proviso that the compound (I) is not selected from the group consisting of
- 1-(3-Chlorophenylamino)-2,3-dihydro-4-methyl-5-phenyl-1H-imidazole-2-thione;
- 1-(2-Chlorophenylamino)-2,3-dihydro-4-methyl-5-phenyl-1H-imidazole-2-thione;
- 1-(4-Chlorophenylamino)-2,3-dihydro-4-methyl-5-phenyl-1H-imidazole-2-thione;
- 1-(phenylamino)-2,3-Dihydro-4-methyl-5-phenyl-1H-imidazole-2-thione;
- 1-(4-nitrophenylamino)-2,3-dihydro-4-methyl-5-phenyl-1H-imidazole-2-thione;
- 1-(4-methylphenylamino)-2,3-dihydro-4-methyl-5-phenyl-1H-imidazole-2-thione;
- 1-(4-methyloxyphenylamino)-2,3-dihydro-4-methyl-5-phenyl-1H-imidazole-2-thione;
- 1-(benzylamino)-2,3-dihydro-4-methyl-5-phenyl-1H-imidazole-2-thione;
- 4-Methyl-5-phenyl-1-phenylamino-1H-imidazole;
- 4-Methyl-5-phenyl-1-(4-nitrophenyl)amino-1H-imidazole;
- 4-Methyl-5-phenyl-1-(4-chlorophenyl)amino-1H-imidazole;
- 4-Methyl-5-phenyl-1-(4-methylphenyl)amino-1H-imidazole; and
- 4-Methyl-5-phenyl-1-(4-methyloxyphenyl)amino-1H-imidazole, said process comprising the steps of reacting an α-haloketone having the formula Q-(CH$_2$)—CO—CHR$_1$X, wherein Q, $R_1$ and n are as defined in formula (I) and X is a halogen atom, first with an alkali thiocyanate and then with a hydrazine derivative having the formula L-(CH$_2$)$_m$—NHNH$_2$, thereby obtaining an N-aminoimidazolethione derivative having the formula (I) wherein $R_2$ is —SH, and further optionally comprising the oxidative reduction of the said N-aminoimidazolethione derivative for preparing a derivative having the formula (I) wherein $R_2$ is hydrogen.

5. A process according to claim 4, further comprising reacting the N-aminoimidazolethione derivative having the formula (I) wherein $R_2$ is —SH with an alkylating or glycosylating agent.

6. A pharmaceutical composition comprising an N-aminoimidazole or N-aminoimidazolethione derivative, a pharmaceutically acceptable salt, a tautomer, an isomer, an ester or a glycosylation product thereof, said derivative being a compound represented by the general formula (I):

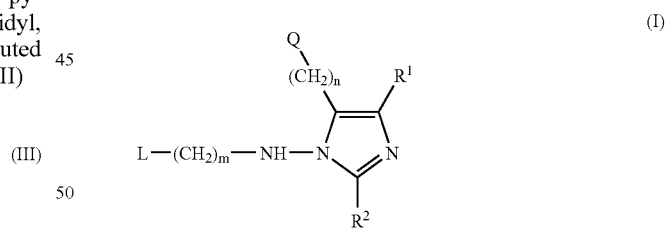

wherein:
- m is zero or 1;
- n is zero or 1;
- $R^1$ is selected from hydrogen, methyl, ethyl, propyl or isopropyl;
- $R^2$ selected from hydrogen or —SH;
- Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, carboxyl, aminocarbonyl, alkylamino-carbonyl, dialkylaminocarbonyl, phenylaminocarbonyl, alkyloxycarbonyl or phenyl;
  - wherein alkyl is a methyl, ethyl, propyl or isopropyl and phenyl is a substituted or unsubstituted phenyl ring represented by the general formula (II);

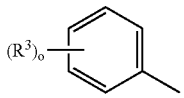
(II)

wherein o is 1 or 2, and R³ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl; and L is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring represented by the general formula (III);

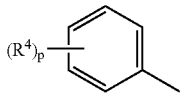
(III)

wherein p is 1 or 2, and R⁴ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl, as an active ingredient in admixture with at least a pharmaceutically acceptable carrier.

7. A pharmaceutical composition according to claim 6, having antiviral activity.

8. A pharmaceutical composition according to claim 6, having activity against HIV (Human Immunodeficiency Virus).

9. A pharmaceutical composition according to claim 6, wherein the said active ingredient is an agent for inhibiting the proliferation of hepatitis B virus, hepatitis C virus or flaviviruses.

10. A pharmaceutical composition according to claim 6, comprising said active ingredient in a concentration range from about 0.1 to about 100% by weight.

11. A pharmaceutical composition according to claim 6, in a form selected from the group consisting of powders, suspensions, solutions, sprays, emulsions, concentrates, granulates, dusts, aerosols, tablets, pellets, ointments and creams.

12. A pharmaceutical composition according to claim 6, further comprising one or more retroviral enzyme inhibitors in respective proportions such as to provide a synergistic effect against a viral infection in a mammal, as a combined preparation for simultaneous, separate or sequential use in retroviral infection therapy.

13. A pharmaceutical composition according to claim 6, further comprising one or more retroviral enzyme inhibitors in respective proportions such as to provide a synergistic effect against a viral infection in a mammal, as a combined preparation for simultaneous, separate or sequential use in retroviral infection therapy, wherein the retroviral enzyme inhibitor is selected from HIV integrase inhibitors, reverse transcriptase inhibitors, nucleoside reverse transcriptase inhibitors, non-nucleoside reverse transcriptase inhibitors and HIV protease inhibitors.

14. A method of treatment of a viral infection in a mammal, comprising administering to the mammal in need of such treatment a therapeutically effective amount of an N-aminoimidazole or N-aminoimidazolethione derivative, a pharmaceutically acceptable salt, a tautomer, an isomer, an ester or a glycosylation product thereof; said derivative being a compound represented by the general formula (I):

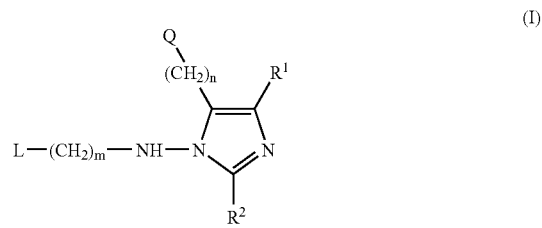
(I)

wherein:
m is zero or 1;
n is zero or 1;
R¹ is selected from hydrogen, methyl, ethyl, propyl or isopropyl;
R² is selected from hydrogen and —SH;
Q is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, carboxyl, aminocarbonyl, alkylamino-carbonyl, dialkylaminocarbonyl, phenylaminocarbonyl, alkyloxycarbonyl or phenyl;
wherein alkyl is a methyl, ethyl, propyl or isopropyl and phenyl is a substituted or unsubstituted phenyl ring represented by the general formula II;

(II)

wherein o is 1 or 2, and R³ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl; and L is selected from 1-naphtyl, 2-naphtyl, biphenyl, 2-pyridyl, 3-pyridyl, 4-pyridyl, 2-pyrimidyl, 4-pyrimidyl, 5-pyrimidyl, thienyl, or a substituted or unsubstituted phenyl ring represented by the general formula III;

(III)

wherein p is 1 or 2, and R⁴ is selected from H, F, Cl, Br, I, hydroxy, alkyloxy, amino, alkylamino, dialkylamino, cyano, nitro, carboxyl, aminocarbonyl, alkylaminocarbonyl, alkyloxycarbonyl, methyl, ethyl, propyl, isopropyl or $C_{1-3}$ haloalkyl wherein haloalkyl contains 1 to 4 haloatoms and alkyl is selected from methyl, ethyl, propyl or isopropyl, as an active ingredient.

15. A method of treatment according to claim 14, further comprising administering to the mammal one or more retroviral enzyme inhibitors in respective proportions such as to provide a synergistic effect against viral infection.

16. A method of treatment according to claim 14, wherein the therapeutically effective amount of compound (I) is a retroviral replication inhibiting amount.

17. A method of treatment according to claim 14, further comprising administering to the mammal one or more retroviral enzyme inhibitors in respective proportions such as to provide a synergistic effect against viral infection, wherein the said retroviral enzyme inhibitor is selected from HIV integrase inhibitors, reverse transcriptase inhibitors, nucleoside reverse transcriptase inhibitors, non-nucleoside reverse transcriptase inhibitors and HIV protease inhibitors.

18. A method of treatment according to claim 14, further comprising administering to the mammal one or more retroviral enzyme inhibitors in respective proportions such as to provide a synergistic effect against viral infection, and wherein the compound of formula (I) and the retroviral enzyme inhibitor are administered simultaneously, separately or sequentially.

* * * * *